(12) United States Patent
Taeschler et al.

(10) Patent No.: US 11,739,066 B2
(45) Date of Patent: Aug. 29, 2023

(54) METHOD FOR FLUOROALKYLATION OF ENAMINES

(71) Applicant: Arxada AG, Visp (CH)

(72) Inventors: Christoph Taeschler, Visp (CH); Matthias Beller, Nienhagen (DE); Helfried Neumann, Rostock (DE); Florian Fischer, Rostock (DE); Shaoke Zhang, Rostock (DE); Fei Ye, Rostock (DE); Stefan Ellinger, Visp (CH); Florencio Zaragoza Doerwald, Buochs (CH)

(73) Assignee: Arxada AG, Visp (CH)

( * ) Notice: Subject to any disclaimer, the term of this patent is extended or adjusted under 35 U.S.C. 154(b) by 0 days.

(21) Appl. No.: 17/618,110

(22) PCT Filed: Jun. 12, 2020

(86) PCT No.: PCT/EP2020/066351
§ 371 (c)(1),
(2) Date: Dec. 10, 2021

(87) PCT Pub. No.: WO2020/249759
PCT Pub. Date: Dec. 17, 2020

(65) Prior Publication Data
US 2022/0204464 A1    Jun. 30, 2022

Related U.S. Application Data

(60) Provisional application No. 62/860,393, filed on Jun. 12, 2019.

(30) Foreign Application Priority Data

Jun. 12, 2019  (EP) .................................. 19179702
Jul. 5, 2019   (EP) .................................. 19184587
Jul. 16, 2019  (EP) .................................. 19186599

(51) Int. Cl.
| | | |
|---|---|---|
| *C07D 295/073* | (2006.01) | |
| *C07C 45/68* | (2006.01) | |
| *C07C 67/343* | (2006.01) | |
| *C07D 295/067* | (2006.01) | |
| *C07D 317/72* | (2006.01) | |
| *C07D 335/02* | (2006.01) | |
| *C07D 451/06* | (2006.01) | |
| *C07J 1/00* | (2006.01) | |

(52) U.S. Cl.
CPC .......... *C07D 295/073* (2013.01); *C07C 45/68* (2013.01); *C07C 67/343* (2013.01); *C07D 295/067* (2013.01); *C07D 317/72* (2013.01); *C07D 335/02* (2013.01); *C07D 451/06* (2013.01); *C07J 1/0055* (2013.01); *C07J 1/0062* (2013.01); *C07C 2601/08* (2017.05); *C07C 2601/14* (2017.05)

(58) Field of Classification Search
None
See application file for complete search history.

(56) References Cited

U.S. PATENT DOCUMENTS 9,809,596 B1    11/2017   Taeschler et al.

FOREIGN PATENT DOCUMENTS

| JP | 2017533916 | 11/2017 |
|---|---|---|
| WO | WO 2016/071425 | 5/2016 |
| WO | WO2019020726 | 1/2019 |

OTHER PUBLICATIONS

Cantacuzene et al. "Condensation of perfluoroalkyl iodides with unsaturated nitrogen compounds" J. Chem. Soc., Perkin Trans. 1, 1977, pp. 1365-1371.*
Sun et al. "Novel Reactions of Enamines with Perhaloethanes : A Facile Route to β2CF3 Substituted α,β2Unsaturated Ketones" Acta Chimica Sinica, 2003, vol. 61, No. 10, pp. 1641-1645.*
International Search Report and Written Opinion for PCT/EP2020/066351 dated Jun. 30, 2020, 16 pages.
Cao H P et al: "Fluoroalkylation of aromatics: An intramolecular radical cyclization of 4-chloro-1,1,2,2,3,3,4,4-octafluorobutylbenzenes", Journal of Fluorine Chemistry, Elsevier, NL, vol. 127, No. 8, Aug. 1, 2006 (Aug. 1, 2006), pp. 1079-1086.
Dunn C et al: "The Synthesis of Fluorine-Containing Pterins", Tetrahedron, Elsevier Science Publishers, Amsterdam, NL, vol. 52, No. 40,Jan. 1, 1996 (Jan. 1, 1996), 13017-13026.
Gilbert Stork et al: "Enamine Alkylation and Acylation of Carbonyls", J. Am. Chem. Soc. 1963,85,2, 207-222, Jan. 1, 1963 (Jan. 1, 1963), pp. 207-222.
Qingqing Qi et al: "Polyfluoroalkylation of 2-aminothiazoles", Journal of Fluorine Chemistry, Elsevier, NL, vol. 133, Jul. 7, 2011 (Jul. 7, 2011), pp. 115-119.
Thomson et al: "The Stereochemistry of Organometallic Compounds. XXIX* Synthesis of Steroidal 1,4-, 1,3-and 1,6-Diphosphines and Their Evaluation as Ligands in Metal-Catalysed Asymmetric Synthesis", Aust. J. Chem, 40(6) 1083-1106, Jan. 1, 1987 (Jan. 1, 1987), pp. 1083-1106.
Office Action for Japanese Patent Application No. 2021-573431, dated Jun. 1, 2022, 9 pages.
Sun et al., Acta Chimica Sinica, "Novel Reactions of Enamines with Perhaloethanes: a Facil Route to B-Cf3 Substituted z, B-Unsatured Ketones", 2003, v.61, pp. 1641-1645.
International Preliminary Report for Patentability for PCT/EP2020/066351 dated Feb. 24, 2021, 33 pages.

* cited by examiner

*Primary Examiner* — Joseph R Kosack
(74) *Attorney, Agent, or Firm* — Dority & Manning, P.A.

(57) ABSTRACT

The invention discloses a method for fluoroalkylation of enamines with a fluoro alkyl halide in the presence of a base.

18 Claims, No Drawings

METHOD FOR FLUOROALKYLATION OF ENAMINES

RELATED APPLICATIONS

The present application is the national stage entry of International Patent Application No. PCT/EP2020/066351 having a filing date of Jun. 12, 2020, which claims priority to U.S. Provisional Patent Application No. 62/860,393 having a filing date of Jun. 12, 2019, European Patent Application No. 19 179 702.6 having a filing date of Jun. 12, 2019, European Patent Application No. 19 184 587.4 having a filing date of Jul. 5, 2019, and European Patent Application No. 19 186 599.7 having a filing date of Jul. 16, 2019, which are incorporated herein by reference.

The invention discloses a method for fluoroalkylation of enamines with a fluoro alkyl halide in the presence of a base.

BACKGROUND OF THE INVENTION

Organofluorine chemistry plays an important role in medicinal, agricultural, and material sciences and fields. Fluoroalkyl groups have strong effects such as high stability and lipophilicity, in addition, longer fluoroalkyl groups have high water and oil resistance and low friction.

Loy, R. N., et al., Organic Letters 2011, 13, 2548-2551, discloses Pd-catalyzed coupling of $CF_3$—I with benzene in 26% GC yield.

According to Table 1 entry 10 the coupling of $C_6F_{13}I$ provided 81% yield. But a repetition of this experiment with the bromide instead of the iodide provided less than 1% yield, see Comparative Example herein.

There was a need for a homogenously catalyzed method for the preparation of fluoro alkylated compounds such as ketones by alpha C—H fluoro alkylation, which provides satisfactory yields but does not need Pd catalysis. The method should not be restricted to iodides as alkylating agents only, but should also work with bromides.

Unexpectedly a method for fluoroalkylation of enamines with fluoro alkyl halides was found that surprisingly doesn't even need any metal catalysis. Enamines are easily accessible by the known reaction of a keton with a secondary amine on one hand, on the other hand enamines represent a huge variety of substrates which, when fluoro alkylated, can be used for many purposes and provide an excellent source of intermediates suitable for the use in the areas of pharmaceuticals, agro chemicals and material sciences.

Abbreviations and Definitions

In this text, the following meanings are used, if not otherwise stated:
alkyl linear or branched alkyl, preferably linear
eq, equiv equivalent
"linear" and "n-" are used synonymously with respect to the respective isomers of alkanes
"wt %", "% by weight" and "weight-%" are used synonymously and mean percent by weight

SUMMARY OF THE INVENTION

Subject of the invention is a method for a fluoroalkylation of an enamine ENAM by a reaction REAC2, wherein
ENAM is reacted with a fluoro alkyl halide FAHALIDE in the presence of a base BAS;
wherein
FAHALIDE is a compound of formula (FAHALIDE);

$$X2-R3-X1 \quad \text{(FAHALIDE)}$$

R3 is $C_{1-20}$ alkylene, wherein in the alkylene chain at least one of the hydrogens is substituted by F;
X1 is Cl, Br or I;
X2 is C(O)—$OC_{1-4}$ alkyl, F, Br or H;
BAS is selected from the group consisting of $Na_3PO_4$, $Na_2HPO_4$, $K_3PO_4$, $K_2HPO_4$, $Na_2CO_3$, $NaHCO_3$, $K_2CO_3$, $KHCO_3$, $Cs_2CO_3$, $CsHCO_3$, NaOH, KOH, NaOtBu, KOtBu, $NEt_3$, and DBU.

DETAILED DESCRIPTION OF THE INVENTION

Preferably, the reaction REAC2 is performed in the absence of a metal catalyst, in particular a Pd catalyst.
Preferably, said fluoroalkylation of said enamine ENAM by a reaction REAC2 occurs at a carbon atom of said ENAM (C-fluoroalkylation).
Preferably, BAS is selected from the group consisting of $K_3PO_4$, $K_2CO_3$, $Cs_2CO_3$, KOH, KOtBu, $NEt_3$, and DBU.
Preferably, R3 is $C_{1-15}$ alkylene, wherein in the alkylene chain at least one of the hydrogens is substituted by F;
more preferably, R3 is $C_{1-10}$ alkylene, wherein in the alkylene chain at least one of the hydrogens is substituted by F.
Preferably,
X1 is Br or I;
more preferably,
X1 is I.
Preferably,
X2 is C(O)—$OC_{1-4}$ alkyl, F or Br.
Preferably,
X1 is Br or I; and
X2 is C(O)—$OC_{1-4}$ alkyl, F or Br;
more preferably,
X1 is I; and
X2 is C(O)—$OC_{1-4}$ alkyl, F or Br.
Especially, FAHALIDE is selected from the group consisting of $C_{1-20}$ alkyl-X1, Br—$(CF_2)_{n3}$—Br, EtO—C(O)—$CF_2$—X1, $F_3C$—$CH_2$—X1, and $F_3C$—C(Cl)H—X1;
more especially, FAHALIDE is selected from the group consisting of $C_{1-15}$ alkyl-X1, Br—$(CF_2)_{n3}$—Br, EtO—C(O)—$CF_2$—X1, $F_3C$—$CH_2$—X1, and $F_3C$—C(Cl)H—X1;
even more especially, FAHALIDE is selected from the group consisting of $C_{1-10}$ alkyl-X1, Br—$(CF_2)_{n3}$—Br, EtO—C(O)—$CF_2$—X1, $F_3C$—$CH_2$—X1, and $F_3C$—C(Cl)H—X1;
with n3 being an integer of 2 to 10;
preferably, n3 is 2, 3, 4, 5, 6;
more preferably, n3 is 2, 4 or 6;
even more preferably, n3 is 4;
wherein in the alkyl at least one of the C atoms is substituted by F.
In particular, FAHALIDE is selected from the group consisting of $F_{21}C_{10}$—I, $F_{21}C_{10}$—Br, $F_{19}C_9$—I, $F_{19}C_9$—Br, $F_{17}C_8$—I, $F_{17}C_8$—Br, $F_{13}C_6$—I, $F_{13}C_6$—Br, $F_9C_4$—I, $F_9C_4$—Br, $F_7C_3$—I, $F_7C_3$—Br, $F_3C$—I, $F_3C$—Br, Br—$(CF_2)_6$—Br, Br—$(CF_2)_4$—Br, Br—$(CF_2)_2$—Br, EtO—C(O)—$CF_2$—I, EtO—C(O)—$CF_2$—Br, $F_3C$—$CH_2$—$C_1$, $F_3C$—C($C_1$)H—I and $F_3C$—C(Cl)H—Br;
more in particular, FAHALIDE is selected from the group consisting of $F_{21}C_{10}$—I, $F_{19}C_9$—I, $F_{17}C_8$—I, $F_{13}C_6$—I, $F_9C_4$—I, $F_7C_3$—I, $F_{19}C_9$—Br, $F_{17}C_8$—Br, $F_7C_3$—Br, F₃C—Br, Br—(CF₂)₄—Br, EtO—C(O)—CF₂—Br, F₃C—CH₂—C₁, and F₃C—C(Cl)H—Br.

In one embodiment, said alkylene, that is represented by R3, wherein in the alkylene chain at least one of the hydrogens is substituted by F, is a perfluoroalkylene.

In one embodiment, said alkyl in the definition of FAHA-LIDE, wherein in said alkyl at least one of the C atoms is substituted by F, is a perfluoroalkyl.

The term "alkylene" as it is used in instant invention for the definition of R3, with R3 being an alkylene, wherein in the alkylene at least one of the hydrogens is substituted by F, means an alkyl residue which is substituted by X1 and by X2; so FAHALIDE is an alkane substituted by X1 and by X2, wherein at least one of the hydrogens of the alkane is substituted by F.

ENAM may be any enamine formed by a reaction of a secondary amine with a ketone. In the context of the present invention, the definition of "enamine" preferably excludes 2-aminothiazoles, more preferably it excludes thiazoles, even more preferably it excludes the situation where the enamine group is part of an aromatic system, and most preferably it excludes α,β-unsaturated imines (whether part of an aromatic system or otherwise).

Preferably, the fluoroalkylation of said enamine ENAM by a reaction REAC2 occurs at a carbon atom of said ENAM (C-fluoroalkylation). More preferably, the carbon atom at which the C-fluoroalkylation occurs is a carbon atom directly adjacent to the carbonyl group of the ketone (α-carbon) which was reacted with a secondary amine to obtain the enamine ENAM.

ENAM may be a compound of formula (ENAM);

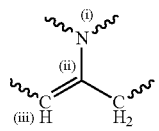

(ENAM)

wherein
the N atom depicted with (i) is a tertiary, non-aromatic N atom;
the C atoms depicted with (ii) and (iii) are non-aromatic C atoms.

ENAM may be a compound of formula (ENAM-I);

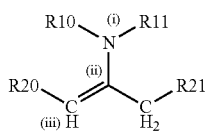

(ENAM-I)

wherein
the N atom depicted with (i) is a tertiary, non-aromatic N atom;
the C atoms depicted with (ii) and (iii) are non-aromatic C atoms;
R20 and R21 are identical or different and selected from the group consisting of H, $C_{1-10}$ alkyl, C(O)—$C_{1-4}$ alkyl, COOH, C(O)—O—$C_{1-4}$ alkyl;
or
R20 and R21 form together with the 3 C atoms in-C$^{(ii)}$H═C$^{(ii)}$(N$^{(iii)}$(R10)R11)-CH₂—, which connect R20 and R21 and with (i), (ii) and (iii) as defined herein, a 5, 6 or 7 membered carbocyclic or heterocyclic, non-aromatic ring RINGA;

the 5 membered RINGA being a ring RINGA-V as depicted in formula (RINGA-V), the 6 membered RINGA being a ring RINGA-VI as depicted in formula (RINGA-VI), and the 7 membered RINGA being a ring RINGA-VII as depicted in formula (RINGA-VII);

(RINGA-V)

(RINGA-VI)

(RINGA-VII)

wherein
each of the two endocyclic C atoms depicted with (1) and (2) in case of RINGA-V,
each of the three endocyclic C atoms depicted with (1), (2) and (3) in case of RINGA-VI, and
each of the four endocyclic C atoms depicted with (1), (2), (3) and (4) in case of RINGA-VII
may be exchanged for a heteroatom O, N or S, said N may be unsubstituted or substituted by a substituent selected from the group consisting of $C_{1-10}$ alkyl, C(O)—$C_{1-4}$ alkyl, and phenyl;

any of the bonds connecting the endocyclic atoms depicted with (1), (2), (3) or (4) in RINGA-V, RINGA-VI and RINGA-VII respectively may be a single or a double bond;

any of the endocyclic C atoms depicted with (1), (2), (3) or (4) in RINGA-V, RINGA-VI and RINGA-VII respectively may be unsubstituted or substituted by one or two identical or different substituents selected from the group consisting of $C_{1-10}$ alkyl, C(O)—$C_{1-4}$ alkyl, COOH, C(O)—O—$C_{1-4}$ alkyl, CN, phenyl, N(R12)R13, and oxo, or may be a carbonyl protected with ethylene glycol;

the two endocyclic C atoms depicted with (1) and (4) in RINGA-VII may be connected by —CH₂— or by —N(R30)-;

R30 may be $C_{1-4}$ alkyl, phenyl or benzyl;

R12 and R13 are identical or different and selected from the group consisting of H, $C_{1-10}$ alkyl, phenyl, and C(O)—$C_{1-4}$ alkyl;

or
R20 and R21 together with the 3 C atoms in the —C$^{(ii)}$H=C$^{(i)}$(N$^{(iii)}$(R10)R11)-CH$_2$— of formula (ENAM-I), which connect R20 and R21 and with (i), (ii) and (iii) as defined herein, are part of a steroid ring system;

R10 and R11 are identical or different and selected from the group consisting of C$_{1-10}$ alkyl and phenyl;

or

R10 and R11 form together with the N atom, which connects R10 and R11, a 5, 6 or 7 membered heterocyclic, non-aromatic ring RINGB;

the 5 membered RINGB being a ring RINGB-V as depicted in formula (RINGB-V), the 6 membered RINGB being a ring RINGB-VI as depicted in formula (RINGB-VI), and the 7 membered RINGB being a ring RINGB-VII as depicted in formula (RINGB-VII);

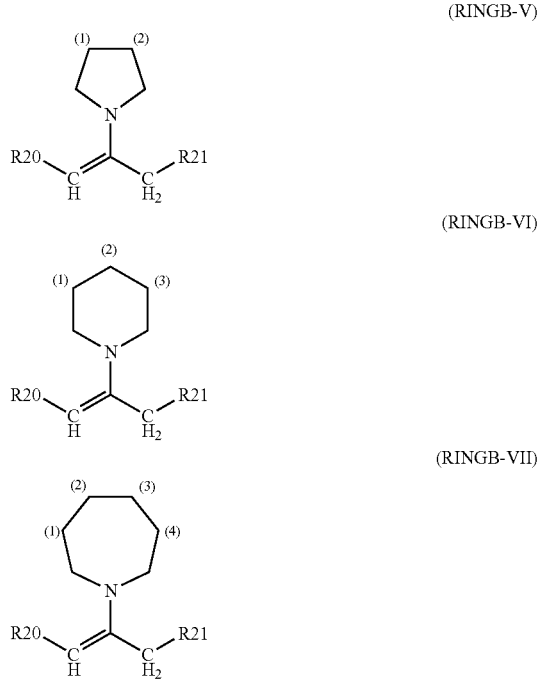

(RINGB-V)

(RINGB-VI)

(RINGB-VII)

wherein each of the two endocyclic C atoms depicted with (1) and (2) in case of RINGB-V, each of the three endocyclic C atoms depicted with (1), (2) and (3) in case of RINGB-VI, and each of the four endocyclic C atoms depicted with (1), (2), (3) and (4) in case of RINGB-VII may be exchanged for a heteroatom O, N or S said N may be unsubstituted or substituted by a substituent selected from the group consisting of C$_{1-10}$ alkyl, C(O)—C$_{1-4}$ alkyl, and phenyl;

any of the bonds connecting the endocyclic atoms depicted with (1), (2), (3) or (4) in RINGB-V, RINGB-VI and RINGB-VII respectively may be a single or a double bond;

any of the endocyclic C atoms depicted with (1), (2), (3) or (4) in RINGB-V, RINGB-VI and RINGB-VII respectively may be unsubstituted or substituted by one or two identical or different substituents selected from the group consisting of C$_{1-10}$ alkyl, C(O)—C$_{1-4}$ alkyl, COOH, C(O)—O—C$_{1-4}$ alkyl, CN, phenyl, N(R14)R15, and oxo, or may be a carbonyl protected with ethylene glycol;

R14 and R15 are identical or different and selected from the group consisting of H, C$_{1-10}$ alkyl, phenyl, and C(O)—C$_{1-4}$ alkyl.

The N atom depicted with (i) in ENAM-I is the same N atom as depicted with (i) in ENAM, and the C atoms depicted with (ii) and (iii) in ENAM-I are the same C atoms as depicted with (ii) and (iii) in ENAM.

When R20 and R21 together with the 3 C atoms in the —C$^{(ii)}$H=C$^{(i)}$(N$^{(iii)}$(R10)R11)-CH$_2$— of formula (ENAM-I), which connect R20 and R21 and with (i), (ii) and (iii) as defined herein, are part of a steroid ring system, said steroid ring system may have gonane as steroid nucleus with a carbonyl (oxo substituent) at C-3. Ring A in the steroid ring system with gonane as steroid nucleus and with a carbonyl (oxo substituent) at C-3 may be saturated. ENAM-I is formed by a reaction of a secondary amine with this carbonyl at C-3.

The steroid ring system with a carbonyl (oxo substituent) at C-3 may be cholesterone, dihydrocholesterone, dihydrotestosterone, dihydroprogesterone, dihydrocortisol, dihydrocortisone, dihydronorethisterone, dihydroaldosterone, dihydrocorticosterone, dihydroandrostenedione and the like. Preferably, R20 and R21 are identical or different and selected from the group consisting of H, C$_{1-4}$ alkyl, C(O)—C$_{1-2}$ alkyl, COOH, C(O)—O—C$_{1-2}$ alkyl;

or one of the two endocyclic C atoms depicted with (1) and (2) in case of RINGA-V, one or two of the three endocyclic C atoms depicted with (1), (2) and (3) in case of RINGA-VI, and one or two of the four endocyclic C atoms depicted with (1), (2), (3) and (4) in case of RINGA-VII may be exchanged for a heteroatom O, N or S said N may be unsubstituted or substituted by a substituent selected from the group consisting of C$_{1-4}$ alkyl, C(O)—C$_{1-2}$ alkyl, and phenyl;

one or two the endocyclic C atoms depicted with (1), (2), (3) or (4) in RINGA-V, RINGA-VI and RINGA-VII respectively may be unsubstituted or substituted by one or two identical or different substituents selected from the group consisting of C$_{1-4}$ alkyl, C(O)—C$_{1-2}$ alkyl, C(O)—O—C$_{1-2}$ alkyl, CN, phenyl, N(R12)R13, and oxo, or may be a carbonyl protected with ethylene glycol;

the two endocyclic C atoms depicted with (1) and (4) in RINGA-VII may be connected by —N(R30)-;

R30 may be C$_{1-2}$ alkyl, phenyl or benzyl;

R12 and R13 are identical or different and selected from the group consisting of H, C$_{1-4}$ alkyl, phenyl, and C(O)—C$_{1-2}$ alkyl;

or

R20 and R21 together with the 3 C atoms in the —C$^{(ii)}$H=C$^{(i)}$(N$^{(iii)}$(R10)R11)-CH$_2$— of formula (ENAM-I), which connect R20 and R21 and with (i), (ii) and (iii) as defined herein, are part of a steroid ring system.

Preferably, R10 and R11 are identical or different and selected from the group consisting of C$_{1-4}$ alkyl and phenyl;

or

R10 and R11 form together with the N atom, which connects R10 and R11, RINGB-V or RINGB-VI;

wherein one of the two endocyclic C atoms depicted with (1) and (2) in case of RINGB-V, and one or two of the three endocyclic C atoms depicted with (1), (2) and (3) in case of RINGB-VI
may be exchanged for a heteroatom O, N or S said N may be unsubstituted or substituted by a substituent selected from the group consisting of $C_{1-4}$ alkyl, $C(O)$—$C_{1-2}$ alkyl, and phenyl;
one or two of the endocyclic C atoms depicted with (1), (2) or (3) in RINGB-V and RINGB-VI respectively may be unsubstituted or substituted by one or two identical or different substituents selected from the group consisting of $C_{1-4}$ alkyl, $C(O)$—$C_{1-2}$ alkyl, $C(O)$—O—$C_{1-2}$ alkyl, CN, phenyl, N(R14)R15, and oxo, or may be a carbonyl protected with ethylene glycol;
R14 and R15 are identical or different and selected from the group consisting of IT, $C_{1-4}$ alkyl, phenyl, and $C(O)$—$C_{1-2}$ alkyl.
More preferably, R10 and R11 are identical or different and selected from the group consisting of $C_{1-4}$ alkyl and phenyl;
or
R10 and R11 form together with the N atom, which connects R10 and R11, RINGB-V or RINGB-VI;
wherein
one of the two endocyclic C atoms depicted with (1) and (2) in case of RINGB-V, and
one of the three endocyclic C atoms depicted with (1), (2) and (3) in case of RINGB-VI
may be exchanged for a heteroatom O;
one or two of the endocyclic C atoms depicted with (1), (2) or (3) in RINGB-V and RINGB-VI respectively may be unsubstituted or substituted by one or two identical or different substituents selected from the group consisting of $C_{1-4}$ alkyl, N(R14)R15, and oxo, or may be a carbonyl protected with ethylene glycol;
R14 and R15 are identical or different and selected from the group consisting of IT, $C_{1-4}$ alkyl, phenyl, and $C(O)$—$C_{1-2}$ alkyl.
Even more preferably, R10 and R11 are identical or different and selected from the group consisting of $C_{1-4}$ alkyl and phenyl;
or
R10 and R11 form together with the N atom, which connects R10 and R11, RINGB-V or RINGB-VI;
wherein
the endocyclic C atom depicted with (2) in case of RINGB-VI may be exchanged for a heteroatom O.

Embodiments of ENAM are

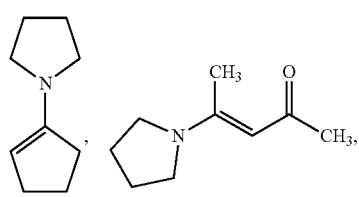

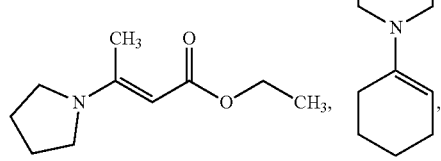

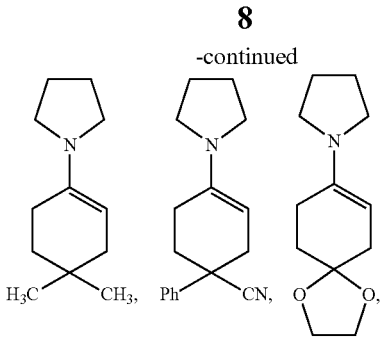

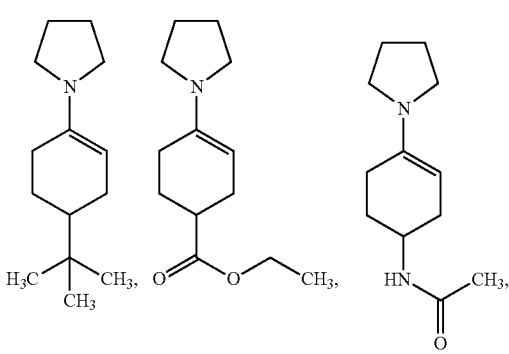

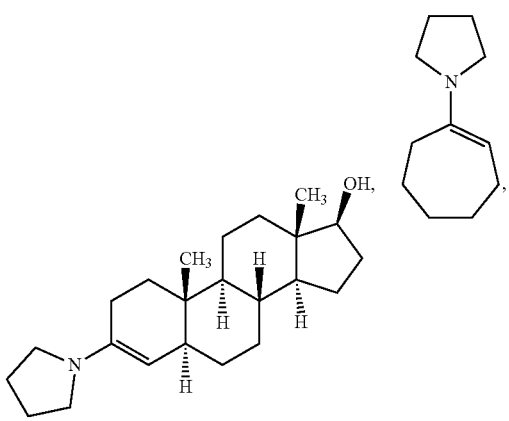

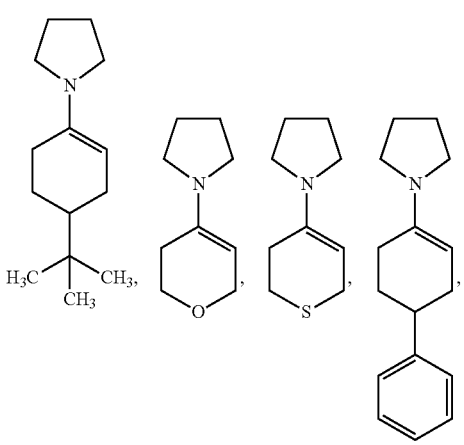

-continued

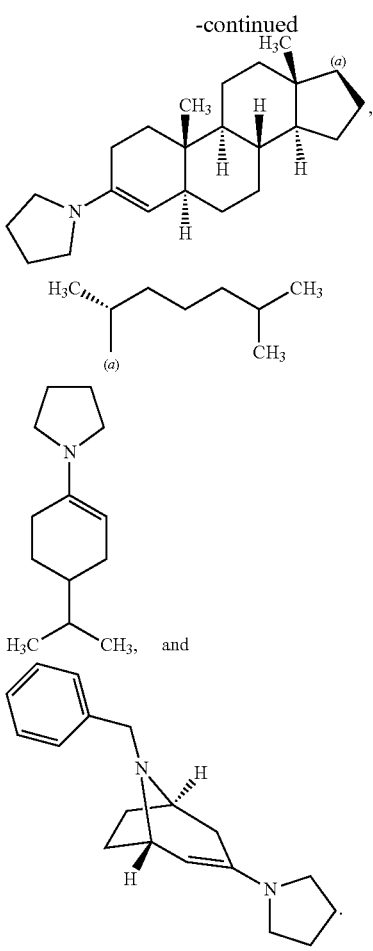

The reaction product of REAC2 is a fluoroalkylated ENAM.

The molar amount of FAHALIDE in REAC2 may be from 0.01 to 10 fold, more preferably from 0.05 to 5 fold, even more preferably from 0.1 to 4 fold, especially from 0.1 to 3 fold, more especially from 0.2 to 2.1 fold, of the molar amount of ENAM.

The molar amount of BAS in REAC2 may be from 0.1 to 10 fold, preferably from 0.2 to 5 fold, even more preferably from 0.3 to 4 fold, especially from 0.4 to 3.1 fold, of the molar amount of ENAM.

REAC2 may be done in a solvent SOLV2, SOLV2 may be THF, Et$_2$O, toluene, Heptane, acetonitrile, DCM or ethyl acetate;

preferably, REAC2 may be done in a solvent SOLV2, SOLV2 may be THF, Et$_2$O, toluene, Heptane, acetonitrile or DCM.

The amount of SOLV2 in REAC2 may be from 2 to 100 fold, preferably from 3 to 50 fold, even more preferably from 3 to 25 fold, especially from 3 to 15 fold, of the weight of ENAM.

The reaction temperature TEMP2 of REAC2 may be from −10 to 150° C., preferably, from −5 to 120° C., more preferably from 0 to 100° C., even more preferably from 10 to 90° C.

The reaction time TIME2 of REAC2 may be from 1 to 100 h, preferably, from 2 to 100 h, more preferably from 5 to 100 h, even more preferably from 10 to 100 h.

REAC2 may be done under ambient pressure or under elevated pressure; the pressure of REAC2 may result from or be determined by the combination of the chosen TEMP2 together with the vapor pressure of the reaction mixture.

REAC2 may be done under inert atmosphere, the inert atmosphere may be provided by nitrogen or argon.

REAC2 is preferably done in the absence of water or at least with a minimized amount of water present. In order to minimize the amount of water present in REAC2 various measures can be taken such as drying of any of the substances prior to REAC2, which are present in REAC2, such as substrate, FAHALIDE, BAS or any solvent; or REAC2 may be done in the presence of a an drying agent DRYAG; DRYAG may be selected from the group consisting of molecular sieve or hygroscopic salts such as CaCl$_2$, MgSO$_4$, or Na$_2$SO$_4$;

preferably molecular sieve.

Preferably, a molecular sieve has a pore size of from 2 to 6 angstrom.

A molecular sieve may be a sodium aluminum silicate, such as Na$_{12}$[(AlO$_2$)$_{12}$(SiO$_2$)$_{12}$] xH$_2$O.

Preferably, the amount of DRYAG used in the reaction is from 0.1 to 2 fold, more preferably from 0.1 to 1.5 fold, even more preferably from 0.1 to 1 fold, especially from 0.1 to 0.75 fold, more especially from 0.1 to 0.5 fold, based on the weight of substrate.

ENAM may be prepared with a reaction REAC1 of a secondary amine SEKAM with a ketone KET.

SEKAM may be any secondary amine which is capable for forming an enamine with a ketone.

SEKAM may be a compound of formula (SEKAM);

(SEKAM)

wherein
the N atom depicted with (i) is a secondary, non-aromatic N atom.

SEKAM may be a compound of formula (SEKAM-I);

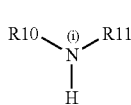

(SEKAM-I)

wherein
the N atom depicted with (i) is a secondary, non-aromatic N atom;
R10 and R11 are as defined herein, also with all their embodiments.

Embodiments of SEKAM are pyrrolidine, morpholine, piperidine, hexamethyldisilazane,
diisopropylamine and diethylamine;
preferably, pyrrolidine and morpholine.

KET may be any ketone which is capable for forming an enamine with a secondary amine.

KET may be a compound of formula (KET);

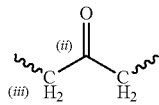

(KET)

wherein
the C atoms depicted with (ii) and (iii) are non-aromatic C atoms.
KET may be a compound of formula (KET-I);

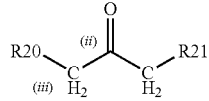
(KET-I)

wherein
the C atoms depicted with (ii) and (iii) are non-aromatic C atoms;
R20 and R21 are as defined herein, also with all their embodiments.

Embodiments of KET are

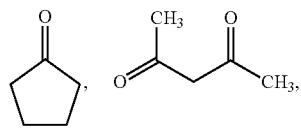

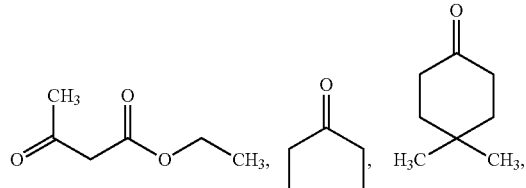

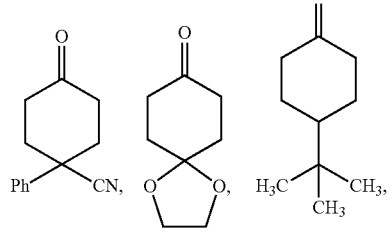

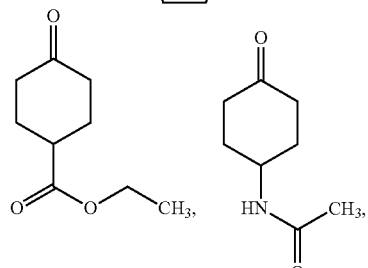

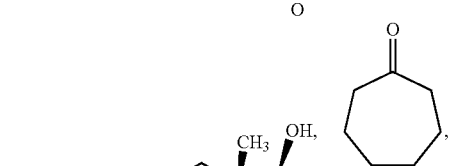

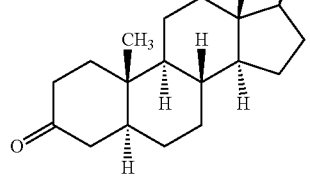

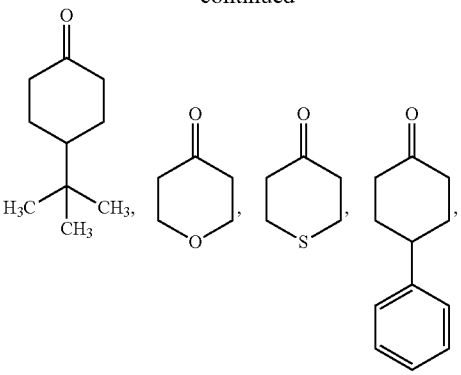

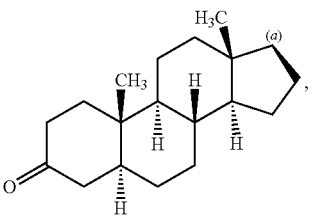

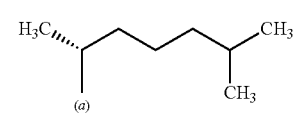

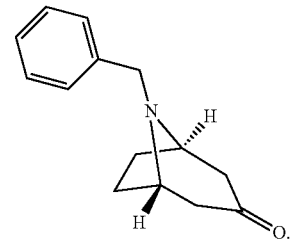

The N atom depicted with (i) in KET-I is the same N atom as depicted with (i) in KET and is the same N atom as depicted with (i) in ENAM and ENAM-I, and
the C atoms depicted with (ii) and (iii) in KET-I are the same C atoms as depicted with (ii) and (iii) in KET and are the same C atoms as depicted with (ii) and (iii) in ENAM and ENAM-I.

The molar amount of SEKAM in REAC1 may be from 1 to 10 fold, preferably from 1 to 5 fold, more preferably from 1 to 4 fold, even more preferably from 1 to 3 fold, especially from 1 to 2.3 fold, of the molar amount of KET.

REAC1 may be done in a solvent SOLV1, SOLV1 may be THF, Et$_2$O, toluene, Heptane, acetonitrile, DCM or ethyl acetate;
preferably, REAC1 may be done in a solvent SOLV1, SOLV1 may be THF, Et$_2$O, toluene, Heptane, acetonitrile or DCM.

The amount of SOLV1 in REAC1 may be from 2 to 100 fold, preferably from 3 to 50 fold, even more preferably from 3 to 25 fold, especially from 3 to 15 fold, of the weight of KET.

The reaction temperature TEMP1 of REAC1 may be from −10 to 150° C., preferably, from −5 to 120° C., more preferably from 0 to 100° C., even more preferably from 10 to 90° C.

The reaction time TIME1 of REAC1 may be from 1 to 100 h, preferably, from 2 to 100 h, more preferably from 5 to 100 h, even more preferably from 10 to 100 h.

REAC1 may be done under ambient pressure or under elevated pressure; the pressure of REAC1 may result from or be determined by the combination of the chosen TEMP1 together with the vapor pressure of the reaction mixture.

REAC1 may be done under inert atmosphere, the inert atmosphere may be provided by nitrogen or argon.

SOLV1 and SOLV2 may be the same.

For TIME1 and TIME2 the same time may be chosen.

For TEMP1 and TEMP2 the same temperature may be chosen.

Preferably, REAC1 and REAC2 are done without intermediate isolation of ENAM.

Preferably, REAC1 and REAC2 are done in the same reaction vessel.

More preferably, REAC1 and REAC2 are done without intermediate isolation of ENAM and are done in the same reaction vessel.

Even more preferably, REAC1 and REAC2 are done without intermediate isolation of ENAM, are done in the same reaction vessel, and KET, SEKAM, FAHALIDE and BAS are all initially mixed together and are thereby all present in the reactions REAC1 and REAC2, in this case TIME1 and TIME2 are identical and TEMP1 and TEMP2 are identical.

After REAC2, the fluoralkylated ENAM may be hydrolyzed with water in a reaction REAC3 to provide SEKAM and a flouralkylated KET.

REAC3 is preferably done under acidic conditions;
said acidic condition may be provided for by the presence of an acid during REAC3;
said acid may any acid known the skilled person which is capable of catalyzing cleavage of an enamine into the respective secondary amine and the ketone under aqueous conditions, such as HCl, $H_2SO_4$, $H_3PO_4$, trifluoro acetic acid, acetic acid;
preferably HCl.

Said acid may be used in form of an aqueous solution.

The molar amount of water in REAC3 may be the same as or greater than the molar amount of ENAM.

The molar amount of said acid in REAC3 may be a catalytic amount with respect to the molar amount of the fluoroalkylated ENAM, or may be the same as or greater than the molar amount of ENAM. For example, 1 N aqueous HCl may be used.

REAC3 is done by mixing the fluoroalkylated ENAM with water and optionally with said acid. Said mixing is preferably done after REAC2.

REAC3 may be done in a solvent SOLV3, SOLV3 may be THF, $Et_2O$, toluene, Heptane, acetonitrile, DCM or ethyl acetate;
preferably, REAC3 may be done in a solvent SOLV3, SOLV3 may be THF, $Et_2O$, toluene, Heptane, acetonitrile or DCM.

The amount of SOLV3 in REAC3 may be from 2 to 100 fold, preferably from 3 to 50 fold, even more preferably from 3 to 25 fold, especially from 3 to 15 fold, of the weight of fluoroalkylated ENAM.

The reaction temperature TEMP3 of REAC3 may be from −10 to 150° C., preferably, from −5 to 120° C., more preferably from 0 to 100° C., even more preferably from 10 to 90° C.

The reaction time TIME3 of REAC3 may be from 15 min to 24 h, preferably, from 30 min to 12 h, more preferably from 30 min to 6 h, even more preferably from 30 min to 3 h.

REAC3 may be done under ambient pressure or under elevated pressure; the pressure of REAC3 may result from or be determined by the combination of the chosen TEMP3 together with the vapor pressure of the reaction mixture.

REAC3 may be done under inert atmosphere, the inert atmosphere may be provided by nitrogen or argon.

SOLV2 and SOLV3 may be the same.

Preferably, REAC2 and REAC3 are done without intermediate isolation of the fluoroalkylated ENAM after REAC2. When REAC2 and REAC3 are done without intermediate isolation of the fluoroalkylated ENAM after REAC2, then the reaction mixture obtained after REAC2 may be mixed with water and optionally with said acid.

Preferably, REAC2 and REAC3 are done in the same reaction vessel.

More preferably, REAC2 and REAC3 are done without intermediate isolation of the fluoroalkylated ENAM after REAC2 and are done in the same reaction vessel.

Preferably, REAC1, REAC2 and REAC3 are done without intermediate isolation of ENAM or of the fluoroalkylated ENAM.

Preferably, REAC1, REAC2 and REAC3 are done in the same reaction vessel.

More preferably, REAC1, REAC2 and REAC3 are done without intermediate isolation of ENAM or of the fluoroalkylated ENAM and are done in the same reaction vessel.

Even more preferably, REAC1, REAC2 and REAC3 are done without intermediate isolation of ENAM or of the fluoroalkylated ENAM, are done in the same reaction vessel, and KET, SEKAM, FAHALIDE and BAS are all initially mixed together and are thereby all present in the reactions REAC1 and REAC2, in this case TIME1 and TIME2 are identical and TEMP1 and TEMP2 are identical.

When REAC1 and REAC2 are done without intermediate isolation of ENAM, then DRYAG may be present in the reactions REAC1 and REAC2.

ENAM after REAC1, the fluoroalkylated ENAM after REAC2 and the fluoroalkylated KET after REAC3 may be isolated according to procedures known to the skilled person.

EXAMPLES

Abbreviations and Definitions

4 A MS 4 Ångström Molecular sieve, CAS 70955-01-0, $Na_{12}[(AlO_2)_{12}(SiO_2)_{12}]$ $xH_2O$, Sigma Aldrich ProdNo. 688363, amount used was 0.5 g of 4 A MS per 0.5 mmol of the limiting reactant $CF_3Ph$ Benzotrifluoride, alpha, alpha, alpha-trifluorotoluene Conv Conversion in mol % with regard to the limiting substance in the reaction (either substrate or FAHALIDE, as the case may be)

DBU 1,8-Diazabicyclo[5.4.0]undec-7-ene

DCM dichloromethane 1,2-DFB 1,2-difluorobenzene 1,4-DFB 1,4-difluorobenzene $Et_2O$ Diethylether KOtBu Potassium tert. butoxide $NEt_3$ Triethylamine THF Tetrahydrofuran Yield Yield with regard to the limiting substance in the reaction (either substrate or FAHALIDE, as the case may be)

Materials

Protocol 1—REAC2

A mixture of the substrate, FAHALIDE, BAS and the solvent (all equivalents and amounts are specified in the respective tables) were placed in a thick-walled pressure tube (Ace pressure tube, Sigma-Aldrich Art. No Z564559). The gas atmosphere in the pressure tube was flushed with argon, the tube was closed with a screw cap and heated (reaction temperature and reaction time are specified in the respective table). The resulting mixture was cooled to room temperature. Solids were removed by centrifugation (3000 rpm, 15 min). The obtained product solution was analyzed by quantitative GC analysis (internal standard hexadecane), $^{19}$F-NMR analysis using the internal standards 1,2-difluorobenzene, 1,4-difluorobenzene or benzotrifluoride, or GC-MS.

Protocol 2—REAC1, REAC2 and REAC3

A mixture of the substrate, FAHALIDE, SEKAM, BAS, DRYAG and the solvent (all equivalents and amounts are specified in the respective table) were placed in a thick-walled pressure tube (Ace pressure tube, Sigma-Aldrich Art. No Z56455964575). The gas atmosphere in the pressure tube was flushed with argon, the tube was closed with a screw cap and heated (reaction temperature and reaction time are specified in the respective tables). The resulting reaction mixture was mixed with 1 N aqueous hydrochloric acid (2 eq) for 1 hour at ambient temperature. The organic phase was then separated and the product was purified by pipette column chromatography using FluoroFlash® reverse phase silica gel (Sigma Aldrich No.: 00866) and a gradient solvent elution (1. MeOH: H$_2$O (4:1, 10 mL) 2. MeOH (100%, 10 mL) 3. acetone (100%, 10 mL) for long chains fluoroalkyl chains (alkyl chain containing 10 or more carbon atoms) or by normal phase silical gel chromatography using silicagel (Sigma Aldrich No.: 236802) and a gradient solvent elution (1. Pentane Ether (100%) 2. Pentane: Diethylether (50%: 50%, 10 ml) for fluoroalkyl chains containing less than 10 carbon atoms.

The obtained product solution was analyzed by quantitative GC analysis (internal standard hexadecane), 19F-NMR analysis using the internal standards 1,2-difluorobenzene, 1,4-difluorobenzene or benzotrifluoride, or GC-MS.

Protocol 3—REAC1 and REAC2

A mixture of the substrate, FAHALIDE, SEKAM, BAS, DRYAG and solvent (all equivalents and amounts are specified in the respective tables) were placed in a thick-walled pressure tube (Ace pressure tube, Sigma-Aldrich Art. No. Z564559). The gas atmosphere in the pressure tube was flushed with argon, the tube was closed with a screw cap and heated (reaction temperature and reaction time are specified in the respective tables). The resulting mixture was cooled to room temperature. Solids were removed by centrifugation (3000 rpm, 15 min). The obtained product solution was analyzed by quantitative GC analysis (internal standard hexadecane), 19F-NMR analysis using the internal standards 1,2-difluorobenzene, 1,4-difluorobenzene or benzotrifluoride, or GC-MS.

Protocol 4—REAC2 and REAC3

A mixture of the substrate, FAHALIDE, BAS and solvent (all equivalents and amounts are specified in the respective tables) were placed in a thick-walled pressure tube (Ace pressure tube, Sigma-Aldrich Art. No. Z564559). The gas atmosphere in the pressure tube was flushed with argon, the tube was closed with a screw cap and heated (reaction temperature and reaction time are specified in the respective table). The resulting mixture was cooled to room temperature and mixed with 1 N aqueous hydrochloric acid for 1 hour. The organic phase was then separated and analyzed by quantitative GC analysis (internal standard hexadecane), 19F-NMR analysis using the internal standards 1,2-difluorobenzene, 1,4-difluorobenzene or benzotrifluoride, or GC-MS.

Details of the examples are given in Tables 1, 2 and 3.

Examples 1 to 28 were done according to Protocol 1—REAC2.

Examples 29 to 72 and 81 were done according to Protocol 2—REAC1, REAC2 and REAC3.

Examples 77 to 80 were done according to Protocol 3—REAC1 and REAC2.

Examples 73 to 76 were done according to Protocol 4—REAC2 and REAC3.

TABLE 1

| Ex | Substrate | FAHALIDE | Product |
|---|---|---|---|
| 1 | (1-pyrrolidinyl cyclopentene) | I-C(CF$_3$)$_2$F | (cyclopentene with pyrrolidinyl and =C(CF$_3$)$_2$) |
| 2 | (1-pyrrolidinyl cyclopentane) | I-C(CF$_3$)$_2$F | (cyclopentene with pyrrolidinyl and =C(CF$_3$)$_2$) |
| 3 | (1-pyrrolidinyl cyclopentene) | I-C(CF$_3$)$_2$F | (cyclopentene with pyrrolidinyl and =C(CF$_3$)$_2$) |

TABLE 1-continued

| Ex | Substrate | FAHALIDE | Product |
|---|---|---|---|
| 4 | 1-(cyclopent-1-en-1-yl)pyrrolidine | I-CF(CF$_3$)$_2$F | pyrrolidinyl-cyclopentenylidene-C(CF$_3$)$_2$ |
| 5 | 1-(cyclopent-1-en-1-yl)pyrrolidine | I-CF(CF$_3$)$_2$F | pyrrolidinyl-cyclopentenylidene-C(CF$_3$)$_2$ |
| 6 | 1-(cyclopent-1-en-1-yl)pyrrolidine | I-CF(CF$_3$)$_2$F | pyrrolidinyl-cyclopentenylidene-C(CF$_3$)$_2$ |
| 7 | 1-(cyclopent-1-en-1-yl)pyrrolidine | I-CF(CF$_3$)$_2$F | pyrrolidinyl-cyclopentenylidene-C(CF$_3$)$_2$ |
| 8 | 1-(cyclopent-1-en-1-yl)pyrrolidine | I-CF(CF$_3$)$_2$F | pyrrolidinyl-cyclopentenylidene-C(CF$_3$)$_2$ |
| 9 | 1-(cyclopent-1-en-1-yl)pyrrolidine | I-CF(CF$_3$)$_2$F | pyrrolidinyl-cyclopentenylidene-C(CF$_3$)$_2$ |
| 10 | 1-(cyclopent-1-en-1-yl)pyrrolidine | I-CF(CF$_3$)$_2$F | pyrrolidinyl-cyclopentenylidene-C(CF$_3$)$_2$ |
| 11 | 1-(cyclopent-1-en-1-yl)pyrrolidine | I-CF(CF$_3$)$_2$F | pyrrolidinyl-cyclopentenylidene-C(CF$_3$)$_2$ |

TABLE 1-continued

| Ex | Substrate | FAHALIDE | Product |
|----|-----------|----------|---------|
| 12 | 1-(cyclopent-1-en-1-yl)pyrrolidine | I-CF(CF₃)₂ with F | pyrrolidine-cyclopentene with =C(CF₃)₂ |
| 13 | 1-(cyclopent-1-en-1-yl)pyrrolidine | I-CF(CF₃)₂ with F | pyrrolidine-cyclopentene with =C(CF₃)₂ |
| 14 | 1-(cyclopent-1-en-1-yl)pyrrolidine | Br-CF₃ | pyrrolidine-cyclopentene with CF₃ |
| 15 | (Z)-4-(pyrrolidin-1-yl)pent-3-en-2-one | I-CF(CF₃)₂ F | pyrrolidine enamine diketone with =C(CF₃)₂ and CH₂ |
| 16 | ethyl (E)-3-(pyrrolidin-1-yl)but-2-enoate | I-CF(CF₃)₂ F | pyrrolidine enamine ester with =C(CF₃)₂ and CH₂ |
| 17 | 4-(cyclohex-1-en-1-yl)morpholine | I-CF(CF₃)₂ F | morpholine cyclohexene with C(CF₃)₂F |
| 18 | 4-(cyclohex-1-en-1-yl)morpholine | I-CF(CF₃)₂ F | morpholine cyclohexene with C(CF₃)₂F |

TABLE 1-continued

| Ex | Substrate | FAHALIDE | Product |
|----|-----------|----------|---------|
| 19 | 4-(cyclohex-1-en-1-yl)morpholine | I–CF(CF$_3$)$_2$ (I-C(CF$_3$)$_2$F) | morpholine-cyclohexene with –C(CF$_3$)$_2$F substituent |
| 20 | 4-(cyclohex-1-en-1-yl)morpholine | I–C(CF$_3$)$_2$F | morpholine-cyclohexylidene with =C(CF$_3$)$_2$ product |
| 21 | 4-(cyclohex-1-en-1-yl)morpholine | Br–CF$_3$ | 2-CF$_3$-cyclohexenyl morpholine |
| 22 | 4-(cyclohex-1-en-1-yl)morpholine | Br–CF$_2$–C$_8$F$_{17}$ | morpholine-cyclohexenyl with –CF$_2$C$_8$F$_{17}$ |
| 23 | 4-(cyclohex-1-en-1-yl)morpholine | I–CF$_2$–C$_8$F$_{17}$ | morpholine-cyclohexenyl with –CF$_2$C$_8$F$_{17}$ |
| 24 | 1-(cyclopent-1-en-1-yl)pyrrolidine | Br–CF$_2$–C$_8$F$_{17}$ | pyrrolidine-cyclopentylidene with =CF(C$_8$F$_{17}$) |
| 25 | 1-(cyclopent-1-en-1-yl)pyrrolidine | Br–CF$_3$ | pyrrolidine-cyclopentenyl with –CF$_3$ |

TABLE 1-continued

| Ex | Substrate | FAHALIDE | Product |
|---|---|---|---|
| 26 | 1-(cyclopent-1-en-1-yl)pyrrolidine | CHBrClCF$_3$ | 1-(5-(2,2,2-trifluoroethylidene)cyclopent-1-en-1-yl)pyrrolidine |
| 27 | 1-(cyclopent-1-en-1-yl)pyrrolidine | BrCF$_2$COOEt | ethyl 2-fluoro-2-(2-(pyrrolidin-1-yl)cyclopent-2-en-1-ylidene)acetate |
| 28 | 1-(cyclopent-1-en-1-yl)pyrrolidine | ClCH$_2$CF$_3$ | 1-(5,5-bis(2,2,2-trifluoroethyl)cyclopent-1-en-1-yl)pyrrolidine |
| 29 | cyclopentanone | ICF$_2$C$_9$F$_{19}$ | 2-(perfluorodecylidene)cyclopentanone (F, C$_9$F$_{19}$) |
| 30 | 4,4-dimethylcyclohexanone | ICF$_2$C$_9$F$_{19}$ | 2-(perfluorodecylidene)-4,4-dimethylcyclohexanone |
| 31 | 4-phenyl-4-cyanocyclohexanone | ICF$_2$C$_9$F$_{19}$ | 2-(perfluorodecylidene)-4-phenyl-4-cyanocyclohexanone |
| 32 | 1,4-dioxaspiro[4.5]decan-8-one | ICF$_2$C$_9$F$_{19}$ | 7-(perfluorodecylidene)-1,4-dioxaspiro[4.5]decan-8-one |
| 33 | 4-tert-butylcyclohexanone | ICF$_2$C$_9$F$_{19}$ | 2-(perfluorodecylidene)-4-tert-butylcyclohexanone |

TABLE 1-continued

| Ex | Substrate | FAHALIDE | Product |
|----|-----------|----------|---------|
| 34 | 4-oxocyclohexane-1-carboxylic acid ethyl ester | I-CF$_2$-C$_9$F$_{19}$ | ethyl 4-oxo-3-(1-fluoro-C$_9$F$_{19}$-methylene)cyclohexane-1-carboxylate |
| 35 | N-(4-oxocyclohexyl)acetamide | I-CF$_2$-C$_9$F$_{19}$ | N-(4-oxo-3-(1-fluoro-C$_9$F$_{19}$-methylene)cyclohexyl)acetamide |
| 36 | 5α-dihydrotestosterone | I-CF$_2$-C$_9$F$_{19}$ | 2-(1-fluoro-C$_9$F$_{19}$-methylene)-5α-dihydrotestosterone |
| 37 | cyclopentanone | I-CF$_2$-C$_9$F$_{19}$ | 2-(1-fluoro-C$_9$F$_{19}$-methylene)cyclopentanone |
| 38 | cyclopentanone | I-CF$_2$-C$_9$F$_{19}$ | 2-(1-fluoro-C$_9$F$_{19}$-methylene)cyclopentanone |
| 39 | cyclopentanone | I-CF$_2$-C$_9$F$_{19}$ | 2-(1-fluoro-C$_9$F$_{19}$-methylene)cyclopentanone |
| 40 | cyclopentanone | I-CF$_2$-C$_9$F$_{19}$ | 2-(1-fluoro-C$_9$F$_{19}$-methylene)cyclopentanone |
| 41 | cyclopentanone | I-CF$_2$-C$_9$F$_{19}$ | 2-(1-fluoro-C$_9$F$_{19}$-methylene)cyclopentanone |
| 42 | cyclopentanone | I-CF$_2$-C$_9$F$_{19}$ | 2-(1-fluoro-C$_9$F$_{19}$-methylene)cyclopentanone |

TABLE 1-continued
| Ex | Substrate | FAHALIDE | Product |
|----|-----------|----------|---------|
| 43 | 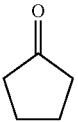 | 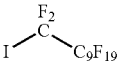 | 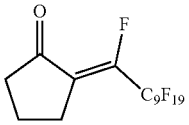 |
| 44 | 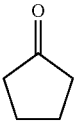 | 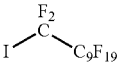 | 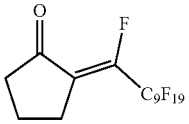 |
| 45 | 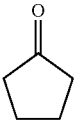 | 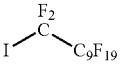 | 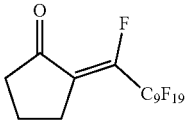 |
| 46 | 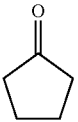 | 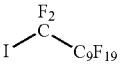 | 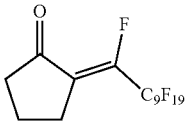 |
| 47 | 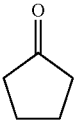 | 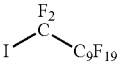 | 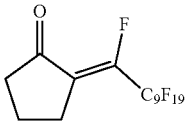 |
| 48 | 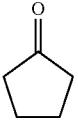 | 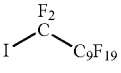 | 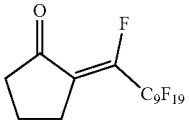 |
| 49 | 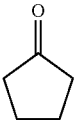 | 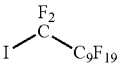 | 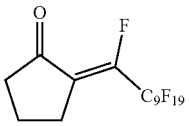 |
| 50 | 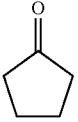 | 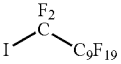 | 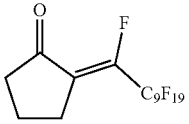 |
| 51 | 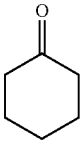 | 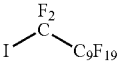 | 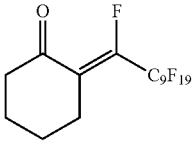 |
| 52 | 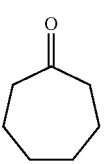 | 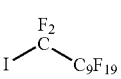 | 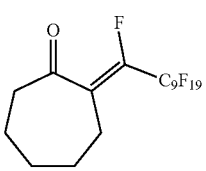 |

TABLE 1-continued

| Ex | Substrate | FAHALIDE | Product |
|---|---|---|---|
| 53 | 4,4-dimethylcyclohexan-1-one | I-CF$_2$-C$_9$F$_{19}$ | 4,4-dimethyl-2-(perfluorodecylidene)cyclohexan-1-one |
| 54 | 4-tert-butylcyclohexan-1-one | I-CF$_2$-C$_9$F$_{19}$ | 4-tert-butyl-2-(perfluorodecylidene)cyclohexan-1-one |
| 55 | 1,4-dioxaspiro[4.5]decan-8-one | I-CF$_2$-C$_9$F$_{19}$ | 1,4-dioxaspiro[4.5]decan-8-one derivative |
| 56 | ethyl 4-oxocyclohexane-1-carboxylate | I-CF$_2$-C$_9$F$_{19}$ | ethyl 4-oxo-3-(perfluorodecylidene)cyclohexane-1-carboxylate |
| 57 | N-(4-oxocyclohexyl)acetamide | I-CF$_2$-C$_9$F$_{19}$ | N-(4-oxo-3-(perfluorodecylidene)cyclohexyl)acetamide |
| 58 | tetrahydro-4H-pyran-4-one | I-CF$_2$-C$_9$F$_{19}$ | 3-(perfluorodecylidene)tetrahydro-4H-pyran-4-one |
| 59 | tetrahydro-4H-thiopyran-4-one | I-CF$_2$-C$_9$F$_{19}$ | 3-(perfluorodecylidene)tetrahydro-4H-thiopyran-4-one |

TABLE 1-continued

| Ex | Substrate | FAHALIDE | Product |
| --- | --- | --- | --- |
| 60 | 4-cyano-4-phenylcyclohexan-1-one | I-CF$_2$-C$_9$F$_{19}$ | 2-(1-fluoro-C$_9$F$_{19}$-methylene)-4-cyano-4-phenylcyclohexan-1-one |
| 61 | 4-phenylcyclohexan-1-one | I-CF$_2$-C$_9$F$_{19}$ | 2-(1-fluoro-C$_9$F$_{19}$-methylene)-4-phenylcyclohexan-1-one |
| 62 | 5α-dihydrotestosterone | I-CF$_2$-C$_9$F$_{19}$ | 2-(1-fluoro-C$_9$F$_{19}$-methylene)-5α-dihydrotestosterone |
| 63 | 5α-cholestan-3-one | I-CF$_2$-C$_9$F$_{19}$ | 2-(1-fluoro-C$_9$F$_{19}$-methylene)-5α-cholestan-3-one |
| 64 | 5α-cholestan-3-one | I-CF$_2$-C$_9$F$_{19}$ | 2-(1-fluoro-C$_3$F$_7$-methylene)-5α-cholestan-3-one |

TABLE 1-continued

| Ex | Substrate | FAHALIDE | Product |
|---|---|---|---|
| 65 | 4-phenylcyclohexanone | $I-CF_2-(CF_2)_2-CF_3$ | 2-(perfluorobut-1-ylidene, with F on α-carbon)-4-phenylcyclohexanone |
| 66 | 4-phenylcyclohexanone | $I-CF_2-(CF_2)_4-CF_3$ | 2-(perfluorohex-1-ylidene)-4-phenylcyclohexanone |
| 67 | 4-phenylcyclohexanone | $I-CF_2-(CF_2)_6-CF_3$ | 2-(perfluorooct-1-ylidene)-4-phenylcyclohexanone |
| 68 | 4-phenylcyclohexanone | $I-C(CH_3)_2-F$ | 2-(1,1-bis(trifluoromethyl)methylene)-4-phenylcyclohexanone |
| 69 | 4-phenylcyclohexanone | $Br-C(CH_3)_2-F$ | 2-(1,1-bis(trifluoromethyl)methylene)-4-phenylcyclohexanone |

TABLE 1-continued

| Ex | Substrate | FAHALIDE | Product |
|---|---|---|---|
| 70 | 4-isopropylcyclohexanone | Br-C(CH₃)₂-F (2-bromo-2-fluoropropane with CH₃ groups shown, but actually CF₃ groups based on product) | 4-isopropyl-2-(1,1,1,3,3,3-hexafluoropropan-2-ylidene)cyclohexanone |
| 71 | 4-phenylcyclohex-3-enone | Br-CF₂-(CF₂)₂-CF₂-Br | 2-(1-fluoro-5-bromo-perfluoropentylidene)-4-phenylcyclohex-3-enone |
| 72 | 4-phenylcyclohexanone | Br-CF₂-(CF₂)₆-CF₂-Br | 2-(1-fluoro-9-bromo-perfluorononylidene)-4-phenylcyclohexanone |
| 73 | 1-morpholinocyclohexene | I-CF(CF₃)₂ | 2-(heptafluoroisopropyl)cyclohexanone |
| 74 | 1-pyrrolidinocyclopentene | I-CF₂-(CF₂)₂-CF₃ | 2-(1-fluoro-perfluoropentylidene)cyclopentanone |
| 75 | 1-pyrrolidinocyclopentene | I-CF₂-(CF₂)₄-CF₃ | 2-(1-fluoro-perfluoroheptylidene)cyclopentanone |

TABLE 1-continued

| Ex | Substrate | FAHALIDE | Product |
|---|---|---|---|
| 76 | (1-pyrrolidinyl-cyclopentene) | $I-CF_2-(CF_2)_6-CF_3$ | (2-(perfluoroalkylidene)cyclopentanone) |
| 77 | cyclopentanone | $I-CF_2-C_9F_{19}$ | (1-pyrrolidinyl-cyclopentene with =CF-C_9F_{19}) |
| 78 | cyclopentanone | $I-CF_2-C_9F_{19}$ | (1-pyrrolidinyl-cyclopentene with =CF-C_9F_{19}) |
| 79 | cyclopentanone | $I-CF_2-C_9F_{19}$ | (1-pyrrolidinyl-cyclopentene with =CF-C_9F_{19}) |
| 80 | cyclopentanone | $I-CF_2-C_9F_{19}$ | (1-pyrrolidinyl-cyclopentene with =CF-C_9F_{19}) |
| 81 | N-benzyl tropinone | $I-CF_2-(CF_2)_4-CF_3$ | N-benzyl tropinone with =CF-C_5F_{11} substituent |

The (a) in Examples 63 and 64 denote where the side chain is bonded to the ring with the indicated stereochemistry.

TABLE 2

| Ex | Substrate Amount | FAHALIDE Amount | SEKAM | SEKAM Amount | BAS | DRYAG | Solvent |
|---|---|---|---|---|---|---|---|
| 1 | 0.5 mmol<br>1 eq | 0.6 mmol<br>1.2 eq | — | — | $K_3PO_4$<br>2 eq | — | THF<br>2 ml |
| 2 | 0.5 mmol<br>1 eq | 0.6 mmol<br>1.2 eq | — | — | $K_2CO_3$<br>2 eq | — | THF<br>2 ml |

TABLE 2-continued

| Ex | Substrate Amount | FAHALIDE Amount | SEKAM | SEKAM Amount | BAS | DRYAG | Solvent |
|---|---|---|---|---|---|---|---|
| 3 | 0.5 mmol<br>1 eq | 0.6 mmol<br>1.2 eq | — | — | Cs$_2$CO$_3$<br>2 eq | — | THF<br>2 ml |
| 4 | 0.5 mmol<br>1 eq | 0.6 mmol<br>1.2 eq | — | — | Cs$_2$CO$_3$<br>2 eq | — | THF<br>2 ml |
| 5 | 0.5 mmol<br>1 eq | 0.6 mmol<br>1.2 eq | — | — | Cs$_2$CO$_3$<br>3 eq | — | THF<br>2 ml |
| 6 | 0.5 mmol<br>1 eq | 0.6 mmol<br>1.2 eq | — | — | KOH<br>2 eq | — | THF<br>2 ml |
| 7 | 0.5 mmol<br>1 eq | 0.6 mmol<br>1.2 eq | — | — | KOtBu<br>2 eq | — | THF<br>2 ml |
| 8 | 0.5 mmol<br>1 eq | 0.6 mmol<br>1.2 eq | — | — | NEt$_3$<br>2 eq | — | THF<br>2 ml |
| 9 | 0.5 mmol<br>1 eq | 0.6 mmol<br>1.2 eq | — | — | DBU<br>2 eq | — | THF<br>2 ml |
| 10 | 0.5 mmol<br>1 eq | 0.6 mmol<br>1.2 eq | — | — | Cs$_2$CO$_3$<br>2 eq | — | Et$_2$O<br>2 ml |
| 11 | 0.5 mmol<br>1 eq | 0.6 mmol<br>1.2 eq | — | — | Cs$_2$CO$_3$<br>2 eq | — | Toluene<br>2 ml |
| 12 | 0.5 mmol<br>1 eq | 0.6 mmol<br>1.2 eq | — | — | Cs$_2$CO$_3$<br>2 eq | — | Heptane<br>2 ml |
| 13 | 0.5 mmol<br>1 eq | 0.6 mmol<br>1.2 eq | — | — | Cs$_2$CO$_3$<br>2 eq | — | Acetonitrile<br>2 ml |
| 14 | 0.5 mmol<br>1 eq | 0.6 mmol<br>1.2 eq | — | — | K$_3$PO$_4$<br>2 eq | — | THF<br>2 ml |
| 15 | 0.5 mmol<br>1 eq | 0.6 mmol<br>1.2 eq | — | — | Cs$_2$CO$_3$<br>2 eq | — | THF<br>2 ml |
| 16 | 0.5 mmol<br>1 eq | 0.6 mmol<br>1.2 eq | — | — | Cs$_2$CO$_3$<br>2 eq | — | THF<br>2 ml |
| 17 | 0.6 mmol<br>1.2 eq | 0.5 mmol<br>1 eq | — | — | Cs$_2$CO$_3$<br>2 eq | — | THF<br>2 ml |
| 18 | 0.6 mmol<br>1.2 eq | 0.5 mmol<br>1 eq | — | — | Cs$_2$CO$_3$<br>3 eq | — | Toluol<br>2 ml |
| 19 | 2 mmol<br>4 eq | 0.5 mmol<br>1 eq | — | — | Cs$_2$CO$_3$<br>3 eq | — | DCM<br>2 ml |
| 20 | 0.6 mmol<br>1.2 eq | 0.5 mmol<br>1 eq | — | — | K$_3$PO$_4$<br>3 eq | — | THF<br>2 ml |
| 21 | 0.6 mmol<br>1.2 eq | 0.5 mmol<br>1 eq | — | — | K$_3$PO$_4$<br>2 eq | — | THF<br>2 ml |
| 22 | 0.6 mmol<br>1.2 eq | 0.5 mmol<br>1 eq | — | — | Cs$_2$CO$_3$<br>2 eq | — | THF<br>2 ml |
| 23 | 0.6 mmol<br>1.2 eq | 0.5 mmol<br>1 eq | — | — | Cs$_2$CO$_3$<br>2 eq | — | THF<br>2 ml |
| 24 | 0.6 mmol<br>1.2 eq | 0.5 mmol<br>1 eq | — | — | Cs$_2$CO$_3$<br>2 eq | — | THF<br>2 ml |
| 25 | 0.6 mmol<br>1.2 eq | 0.5 mmol<br>1 eq | — | — | Cs$_2$CO$_3$<br>2 eq | — | THF<br>2 ml |
| 26 | 0.6 mmol<br>1.2 eq | 0.5 mmol<br>1 eq | — | — | Cs$_2$CO$_3$<br>2 eq | — | THF<br>2 ml |
| 27 | 0.6 mmol<br>1.2 eq | 0.5 mmol<br>1 eq | — | — | Cs$_2$CO$_3$<br>2 eq | — | THF<br>2 ml |
| 28 | 0.6 mmol<br>1.2 eq | 0.5 mmol<br>1 eq | — | — | Cs$_2$CO$_3$<br>2 eq | — | THF<br>2 ml |
| 29 | 0.5 mmol<br>1 eq | 0.6 mmol<br>1.2 eq | pyrrolidine (N-H) | 0.6 mmol<br>1.2 eq | Cs$_2$CO$_3$<br>2 eq | 4A MS | THF<br>2 ml |
| 30 | 0.5 mmol<br>1 eq | 0.6 mmol<br>1.2 eq | pyrrolidine (N-H) | 0.6 mmol<br>1.2 eq | Cs$_2$CO$_3$<br>2 eq | 4A MS | THF<br>2 ml |
| 31 | 0.5 mmol<br>1 eq | 0.6 mmol<br>1.2 eq | pyrrolidine (N-H) | 0.6 mmol<br>1.2 eq | Cs$_2$CO$_3$<br>2 eq | 4A MS | THF<br>2 ml |
| 32 | 0.5 mmol<br>1 eq | 0.6 mmol<br>1.2 eq | pyrrolidine (N-H) | 0.6 mmol<br>1.2 eq | Cs$_2$CO$_3$<br>2 eq | 4A MS | THF<br>2 ml |

TABLE 2-continued

| Ex | Substrate Amount | FAHALIDE Amount | SEKAM | SEKAM Amount | BAS | DRYAG | Solvent |
|---|---|---|---|---|---|---|---|
| 33 | 0.5 mmol 1 eq | 0.6 mmol 1.2 eq | 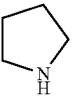 | 0.6 mmol 1.2 eq | Cs$_2$CO$_3$ 2 eq | 4A MS | THF 2 ml |
| 34 | 0.5 mmol 1 eq | 0.6 mmol 1.2 eq | 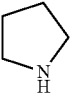 | 0.6 mmol 1.2 eq | Cs$_2$CO$_3$ 2 eq | 4A MS | THF 2 ml |
| 35 | 0.5 mmol 1 eq | 0.6 mmol 1.2 eq | 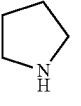 | 0.6 mmol 1.2 eq | Cs$_2$CO$_3$ 2 eq | 4A MS | THF 2 ml |
| 36 | 0.5 mmol 1 eq | 0.6 mmol 1.2 eq | 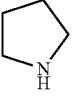 | 0.6 mmol 1.2 eq | Cs$_2$CO$_3$ 2 eq | 4A MS | THF 2 ml |
| 37 | 0.5 mmol 1 eq | 0.6 mmol 1.2 eq | 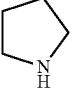 | 0.55 mmol 1.1 eq | Cs$_2$CO$_3$ 2 eq | 4A MS | THF 2 ml |
| 38 | 0.5 mmol 1 eq | 1 mmol 2 eq | 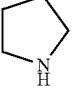 | 1.1 mmol 2.2 eq | Cs$_2$CO$_3$ 2 eq | 4A MS | THF 2 ml |
| 39 | 1 mmol 2 eq | 0.5 mmol 1 eq | 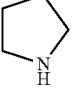 | 1.1 mmol 2.2 eq | Cs$_2$CO$_3$ 2 eq | 4A MS | THF 2 ml |
| 40 | 1.5 mmol 3 eq | 0.5 mmol 1 eq | 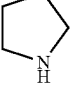 | 1.65 mmol 3.3 eq | Cs$_2$CO$_3$ 2 eq | 4A MS | THF 2 ml |
| 41 | 1 mmol 2 eq | 0.5 mmol 1 eq | 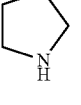 | 1.1 mmol 2.2 eq | Cs$_2$CO$_3$ 1 eq | 4A MS | THF 2 ml |
| 42 | 1 mmol 2 eq | 0.5 mmol 1 eq | 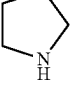 | 1.1 mmol 2.2 eq | Cs$_2$CO$_3$ 0.1 eq | 4A MS | THF 2 ml |
| 43 | 1 mmol 2 eq | 0.5 mmol 1 eq | 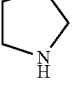 | 1.1 mmol 2.2 eq | K$_3$PO$_4$ 2 eq | 4A MS | THF 2 ml |
| 44 | 1 mmol 2 eq | 0.5 mmol 1 eq | 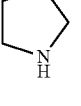 | 1.1 mmol 2.2 eq | K$_3$PO$_4$ 2 eq | 4A MS | THF 2 ml |
| 45 | 1 mmol 2 eq | 0.5 mmol 1 eq | 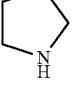 | 1.1 mmol 2.2 eq | NEt$_3$ 2 eq | 4A MS | THF 2 ml |

TABLE 2-continued

| Ex | Substrate Amount | FAHALIDE Amount | SEKAM | SEKAM Amount | BAS | DRYAG | Solvent |
|---|---|---|---|---|---|---|---|
| 46 | 1 mmol 2 eq | 0.5 mmol 1 eq | 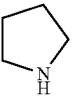 | 1.1 mmol 2.2 eq | DBU 2 eq | 4A MS | THF 2 ml |
| 47 | 1 mmol 2 eq | 0.5 mmol 1 eq | 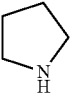 | 1.1 mmol 2.2 eq | $Cs_2CO_3$ 2 eq | 4A MS | Toluene 2 ml |
| 48 | 1 mmol 2 eq | 0.5 mmol 1 eq | 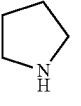 | 1.1 mmol 2.2 eq | $Cs_2CO_3$ 2 eq | 4A MS | Acetonitrile 2 ml |
| 49 | 1 mmol 2 eq | 0.5 mmol 1 eq | 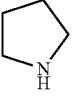 | 1.1 mmol 2.2 eq | $Cs_2CO_3$ 2 eq | 4A MS | Heptane 2 ml |
| 50 | 1 mmol 2 eq | 0.5 mmol 1 eq | 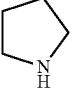 | 1.1 mmol 2.2 eq | $Cs_2CO_3$ 2 eq | 4A MS | THF 2 ml |
| 51 | 1 mmol 2 eq | 0.5 mmol 1 eq | 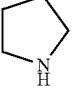 | 1.1 mmol 2.2 eq | $Cs_2CO_3$ 2 eq | 4A MS | THF 2 ml |
| 52 | 1 mmol 2 eq | 0.5 mmol 1 eq | 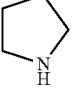 | 1.1 mmol 2.2 eq | $Cs_2CO_3$ 2 eq | 4A MS | THF 2 ml |
| 53 | 1 mmol 2 eq | 0.5 mmol 1 eq | 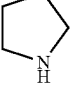 | 1.1 mmol 2.2 eq | $Cs_2CO_3$ 2 eq | 4A MS | THF 2 ml |
| 54 | 1 mmol 2 eq | 0.5 mmol 1 eq | 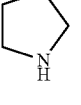 | 1.1 mmol 2.2 eq | $Cs_2CO_3$ 2 eq | 4A MS | THF 2 ml |
| 55 | 1 mmol 2 eq | 0.5 mmol 1 eq | 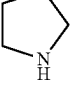 | 1.1 mmol 2.2 eq | $Cs_2CO_3$ 2 eq | 4A MS | THF 2 ml |
| 56 | 1 mmol 2 eq | 0.5 mmol 1 eq | 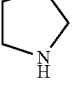 | 1.1 mmol 2.2 eq | $Cs_2CO_3$ 2 eq | 4A MS | THF 2 ml |
| 57 | 1 mmol 2 eq | 0.5 mmol 1 eq | 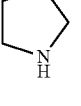 | 1.1 mmol 2.2 eq | $Cs_2CO_3$ 2 eq | 4A MS | THF 2 ml |
| 58 | 1 mmol 2 eq | 0.5 mmol 1 eq | 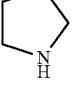 | 1.1 mmol 2.2 eq | $Cs_2CO_3$ 2 eq | 4A MS | THF 2 ml |

TABLE 2-continued

| Ex | Substrate Amount | FAHALIDE Amount | SEKAM | SEKAM Amount | BAS | DRYAG | Solvent |
|---|---|---|---|---|---|---|---|
| 59 | 1 mmol 2 eq | 0.5 mmol 1 eq | 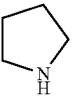 | 1.1 mmol 2.2 eq | Cs$_2$CO$_3$ 2 eq | 4A MS | THF 2 ml |
| 60 | 1 mmol 2 eq | 0.5 mmol 1 eq | 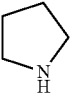 | 1.1 mmol 2.2 eq | Cs$_2$CO$_3$ 2 eq | 4A MS | THF 2 ml |
| 61 | 1 mmol 2 eq | 0.5 mmol 1 eq | 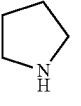 | 1.1 mmol 2.2 eq | Cs$_2$CO$_3$ 2 eq | 4A MS | THF 2 ml |
| 62 | 1 mmol 2 eq | 0.5 mmol 1 eq | 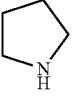 | 1.1 mmol 2.2 eq | Cs$_2$CO$_3$ 2 eq | 4A MS | THF 2 ml |
| 63 | 1 mmol 2 eq | 0.5 mmol 1 eq | 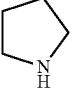 | 1.1 mmol 2.2 eq | Cs$_2$CO$_3$ 2 eq | 4A MS | THF 2 ml |
| 64 | 1 mmol 2 eq | 0.5 mmol 1 eq | 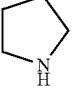 | 1.1 mmol 2.2 eq | Cs$_2$CO$_3$ 2 eq | 4A MS | THF 2 ml |
| 65 | 1 mmol 2 eq | 0.5 mmol 1 eq | 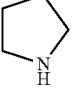 | 1.1 mmol 2.2 eq | Cs$_2$CO$_3$ 2 eq | 4A MS | THF 2 ml |
| 66 | 1 mmol 2 eq | 0.5 mmol 1 eq | 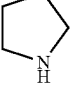 | 1.1 mmol 2.2 eq | Cs$_2$CO$_3$ 2 eq | 4A MS | THF 2 ml |
| 67 | 1 mmol 2 eq | 0.5 mmol 1 eq | 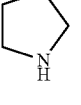 | 1.1 mmol 2.2 eq | Cs$_2$CO$_3$ 2 eq | 4A MS | THF 2 ml |
| 68 | 1 mmol 2 eq | 0.5 mmol 1 eq | 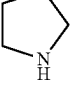 | 1.1 mmol 2.2 eq | Cs$_2$CO$_3$ 2 eq | 4A MS | THF 2 ml |
| 69 | 1 mmol 2 eq | 0.5 mmol 1 eq | 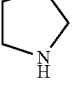 | 1.1 mmol 2.2 eq | Cs$_2$CO$_3$ 2 eq | 4A MS | THF 2 ml |
| 70 | 1 mmol 2 eq | 0.5 mmol 1 eq | 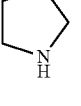 | 1.1 mmol 2.2 eq | Cs$_2$CO$_3$ 2 eq | 4A MS | THF 2 ml |
| 71 | 1 mmol 2 eq | 0.5 mmol 1 eq | 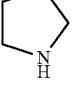 | 1.1 mmol 2.2 eq | Cs$_2$CO$_3$ 2 eq | 4A MS | THF 2 ml |

TABLE 2-continued

| Ex | Substrate Amount | FAHALIDE Amount | SEKAM | SEKAM Amount | BAS | DRYAG | Solvent |
|---|---|---|---|---|---|---|---|
| 72 | 1 mmol / 2 eq | 0.5 mmol / 1 eq | pyrrolidine | 1.1 mmol / 2.2 eq | $Cs_2CO_3$ / 2 eq | 4A MS | THF / 2 ml |
| 73 | 0.6 mmol / 1.2 eq | 0.5 mmol / 1 eq | — | — | $Cs_2CO_3$ / 3 eq | — | THF / 2 ml |
| 74 | 0.6 mmol / 1.2 eq | 0.5 mmol / 1 eq | — | — | $Cs_2CO_3$ / 2 eq | — | $Et_2O$ / 2 ml |
| 75 | 0.6 mmol / 1.2 eq | 0.5 mmol / 1 eq | — | — | $Cs_2CO_3$ / 2 eq | — | $Et_2O$ / 2 ml |
| 76 | 0.6 mmol / 1.2 eq | 0.5 mmol / 1 eq | — | — | $Cs_2CO_3$ / 2 eq | — | $Et_2O$ / 2 ml |
| 77 | 1 mmol / 2 eq | 0.5 mmol / 1 eq | pyrrolidine | 1.1 mmol / 2.2 eq | $Cs_2CO_3$ / 2 eq | 4A MS | THF / 2 ml |
| 78 | 1 mmol / 2 eq | 0.5 mmol / 1 eq | pyrrolidine | 1.1 mmol / 2.2 eq | $K_2CO_3$ / 2 eq | 4A MS | THF / 2 ml |
| 79 | 1 mmol / 2 eq | 0.5 mmol / 1 eq | pyrrolidine | 1.1 mmol / 2.2 eq | DBU / 2 eq | 4A MS | THF / 2 ml |
| 80 | 1 mmol / 2 eq | 0.5 mmol / 1 eq | pyrrolidine | 1.1 mmol / 2.2 eq | $Cs_2CO_3$ / 2 eq | 4A MS | Toluene / 2 ml |
| 81 | 1 mmol / 2 eq | 0.5 mmol / 1 eq | pyrrolidine | 1.1 mmol / 2.2 eq | $Cs_2CO_3$ / 2 eq | 4A MS | THF / 2 ml |

TABLE 3

| Ex | Temp. | Reaction time | Conv | yield | Remarks |
|---|---|---|---|---|---|
| 1 | 25° C. | 16 h | | 66% | quantitative GC using Hexadecane as internal standard |
| 2 | 25° C. | 16 h | | 73% | quantitative GC using Hexadecane as internal standard |
| 3 | 25° C. | 16 h | | 83% | quantitative GC using Hexadecane as internal standard |
| 4 | 25° C. | 16 h | | 89% | quantitative GC using Hexadecane as internal standard |
| 5 | 25° C. | 16 h | | 91% | quantitative GC using Hexadecane as internal standard |
| 6 | 25° C. | 16 h | | 60% | quantitative GC using Hexadecane as internal standard |
| 7 | 25° C. | 16 h | | 53% | quantitative GC using Hexadecane as internal standard |
| 8 | 25° C. | 16 h | | 71% | quantitative GC using Hexadecane as internal standard |
| 9 | 25° C. | 16 h | | 42% | quantitative GC using Hexadecane as internal standard |
| 10 | 25° C. | 16 h | | 89% | quantitative GC using Hexadecane as internal standard |
| 11 | 25° C. | 16 h | | 89% | quantitative GC using Hexadecane as internal standard |
| 12 | 25° C. | 16 h | | 89% | quantitative GC using Hexadecane as internal standard |
| 13 | 25° C. | 16 h | | 89% | quantitative GC using Hexadecane as internal standard |
| 14 | 60° C | 96 h | | 33% | $^{19}$F-NMR ($CF_3Ph$) |
| 15 | 25° C. | 16 h | | 45% | GC-MS |
| 16 | 25° C. | 16 h | | 70% | GC-MS |
| 17 | 25° C. | 16 h | 100% | 75% | $^{19}$F-NMR ($CF_3Ph$) |
| 18 | 25° C. | 16 h | 98% | 82% | $^{19}$F-NMR ($CF_3Ph$) |
| 19 | 25° C. | 16 h | 100% | 99% | $^{19}$F-NMR ($CF_3Ph$) |
| 20 | 25° C. | 16 h | 100% | 55% | $^{19}$F-NMR ($CF_3Ph$) additional 16% yield of morpholine-substituted cyclohexene with $C(CF_3)_2F$ group |
| 21 | 60° C | 96 h | | 20% | $^{19}$F-NMR ($CF_3Ph$) |
| 22 | 25° C. | 16 h | | 81% | $^{19}$F-NMR ($CF_3Ph$) |
| 23 | 25° C. | 16 h | | 81% | $^{19}$F-NMR ($CF_3Ph$) |
| 24 | 25° C. | 16 h | | 57% | $^{19}$F-NMR ($CF_3Ph$) |
| 25 | 60° C | 96 h | | 33% | $^{19}$F-NMR ($CF_3Ph$) |
| 26 | 25° C. | 16 h | | 66% | $^{19}$F-NMR ($CF_3Ph$) |

TABLE 3-continued

| Ex | Temp. | Reaction time | Conv | yield | Remarks |
|---|---|---|---|---|---|
| 27 | 25° C. | 16 h | | 64% | $^{19}$F-NMR (CF$_3$Ph) |
| 28 | 25° C. | 16 h | | 40% | $^{19}$F-NMR (CF$_3$Ph) |
| 29 | 80° C. | 18 h | | 50% | Isolated yield, $^{19}$F-NMR (CF$_3$Ph): 62% yield |
| 30 | 80° C. | 18 h | | 58% | Isolated yield identity by $^{19}$F-NMR |
| 31 | 80° C. | 18 h | | 30% | Isolated yield identity by $^{19}$F-NMR |
| 32 | 80° C. | 18 h | | 48% | Isolated yield identity by $^{19}$F-NMR |
| 33 | 80° C. | 18 h | | 48% | Isolated yield identity by $^{19}$F-NMR |
| 34 | 80° C. | 18 h | | 56% | Isolated yield identity by $^{19}$F-NMR |
| 35 | 80° C. | 18 h | | 29% | Isolated yield identity by $^{19}$F-NMR |
| 36 | 80° C. | 18 h | | 46% | Isolated yield identity by $^{19}$F-NMR |
| 37 | 80° C. | 18 h | 100% | 62% | $^{19}$F-NMR (CF$_3$Ph) |
| 38 | 80° C. | 18 h | 100% | 48% | $^{19}$F-NMR (CF$_3$Ph) |
| 39 | 80° C. | 18 h | 100% | 67% | Isolated yield $^{19}$F-NMR (CF$_3$Ph): 80% yield |
| 40 | 80° C. | 18 h | 100% | 76% | $^{19}$F-NMR (CF$_3$Ph) |
| 41 | 80° C. | 18 h | 100% | 28% | $^{19}$F-NMR (CF$_3$Ph) |
| 42 | 80° C. | 18 h | 84% | 40% | $^{19}$F-NMR (CF$_3$Ph) |
| 43 | 80° C. | 18 h | 100% | 45% | $^{19}$F-NMR (CF$_3$Ph) |
| 44 | 80° C. | 18 h | 100% | 67% | $^{19}$F-NMR (CF$_3$Ph) |
| 45 | 80° C. | 18 h | 92% | 22% | $^{19}$F-NMR (CF$_3$Ph) |
| 46 | 80° C. | 18 h | 100% | 73% | $^{19}$F-NMR (CF$_3$Ph) |
| 47 | 80° C. | 18 h | 100% | 58% | $^{19}$F-NMR (CF$_3$Ph) |
| 48 | 80° C. | 18 h | 100% | 41% | $^{19}$F-NMR (CF$_3$Ph) |
| 49 | 80° C. | 18 h | 100% | 31% | $^{19}$F-NMR (CF$_3$Ph) |
| 50 | 50° C. | 18 h | 64% | 40% | $^{19}$F-NMR (CF$_3$Ph) |
| 51 | 80° C. | 18 h | | 60% | isolated yield $^{19}$F-NMR (CF$_3$Ph): 70% yield |
| 52 | 80° C. | 18 h | | 20% | isolated yield $^{19}$F-NMR (CF$_3$Ph): 40% yield |
| 53 | 80° C. | 18 h | | 67% | isolated yield $^{19}$F-NMR (CF$_3$Ph): 75% yield |
| 54 | 80° C. | 18 h | | 74% | isolated yield $^{19}$F-NMR (CF$_3$Ph): 80% yield |
| 55 | 80° C. | 18 h | | 64% | isolated yield $^{19}$F-NMR (CF$_3$Ph): 79% yield |
| 56 | 80° C. | 18 h | | 54% | isolated yield $^{19}$F-NMR (CF$_3$Ph): 76% yield |
| 57 | 80° C. | 18 h | | 31% | isolated yield $^{19}$F-NMR (CF$_3$Ph): 73% yield |
| 58 | 80° C. | 18 h | | 55% | isolated yield $^{19}$F-NMR (CF$_3$Ph): 85% yield |
| 59 | 80° C. | 18 h | | 66% | isolated yield $^{19}$F-NMR (CF$_3$Ph): 76% yield |
| 60 | 80° C. | 18 h | | 52% | isolated yield |
| 61 | 80° C. | 18 h | | 77% | isolated yield $^{19}$F-NMR (CF$_3$Ph): 79% yield |
| 62 | 80° C. | 18 h | | 52% | isolated yield $^{19}$F-NMR (CF$_3$Ph): 52% yield |
| 63 | 80° C. | 18 h | | 48% | isolated yield |
| 64 | 80° C. | 18 h | | 60% | isolated yield $^{19}$F-NMR (CF$_3$Ph): 67% yield |
| 65 | 80° C. | 18 h | | 87% | isolated yield $^{19}$F-NMR (CF$_3$Ph): 88% yield |
| 66 | 80° C. | 18 h | | 80% | isolated yield $^{19}$F-NMR (CF$_3$Ph): 85% yield |
| 67 | 80° C. | 18 h | | 76% | isolated yield $^{19}$F-NMR (CF$_3$Ph): 67% yield |
| 68 | 80° C. | 18 h | | 84% | $^{19}$F-NMR (CF$_3$Ph): 84% yield |
| 69 | 50° C. | 18 h | | 81% | $^{19}$F-NMR (CF$_3$Ph): 81% yield |
| 70 | 50° C. | 18 h | | 82% | $^{19}$F-NMR (CF$_3$Ph): 82% yield |
| 71 | 80° C. | 18 h | | 53% | isolated yield $^{19}$F-NMR (CF$_3$Ph): 57% yield |
| 72 | 80° C. | 18 h | | 52% | isolated yield $^{19}$F-NMR (CF$_3$Ph): 55% yield |
| 73 | 25° C. | 16 h | 100% | 64% | $^{19}$F-NMR (CF$_3$Ph) Usage of CDCh with some humidity Additional yield of 15% of [structure shown] |
| 74 | 80° C. | 18 h | | 71% | isolated yield $^{19}$F-NMR (CF$_3$Ph) |
| 75 | 80° C. | 18 h | | 60% | isolated yield $^{19}$F-NMR (CF$_3$Ph) |
| 76 | 80° C. | 18 h | | 55% | isolated yield $^{19}$F-NMR (CF$_3$Ph) |
| 77 | 80° C. | 18 h | 100% | 80% | $^{19}$F-NMR (CF$_3$Ph) |
| 78 | 80° C. | 18 h | 100% | 67% | $^{19}$F-NMR (CF$_3$Ph) |
| 79 | 80° C. | 18 h | 100% | 73% | $^{19}$F-NMR (CF$_3$Ph) |
| 80 | 80° C. | 18 h | 100% | 58% | $^{19}$F-NMR (CF$_3$Ph) |
| 81 | 80° C. | 18 h | | 30% | isolated yield $^{19}$F-NMR (CF$_3$Ph): 38% yield |

The invention claimed is:

1. A method for a fluoroalkylation of an enamine ENAM by a reaction REAC2, wherein
ENAM is reacted with a fluoro alkyl halide FAHALIDE in the presence of a base BAS;
wherein
FAHALIDE is a compound of formula (FAHALIDE);

$$X2-R3-X1 \quad \text{(FAHALIDE)}$$

R3 is $C_{1-20}$ alkylene, wherein in the alkylene chain at least one of the hydrogens is substituted by F;
X1 is Cl, Br or I;
X2 is C(O)—OC$_{1-4}$ alkyl, F, Br or H;
BAS is selected from the group consisting of Na$_3$PO$_4$, Na$_2$HPO$_4$, K$_3$PO$_4$, K$_2$HPO$_4$, Na$_2$CO$_3$, NaHCO$_3$, K$_2$CO$_3$, KHCO$_3$, Cs$_2$CO$_3$, CsHCO$_3$, NaOH, KOH, NaOtBu, KOtBu, and DBU;
wherein the reaction REAC2 is performed in the absence of a metal catalyst, in the absence of a Pd catalyst;
wherein the fluoroalkylation of said enamine ENAM by a reaction REAC2 occurs at a carbon atom of said ENAM; and
wherein
ENAM is a compound of formula (ENAM);

(ENAM)

wherein
the N atom depicted with (i) is a tertiary, non-aromatic N atom;
the C atoms depicted with (ii) and (iii) are non-aromatic C atoms;

wherein the reaction is between about 16 hours and about 96 hours and the reaction temperature is between about 25° C. and about 80° C.; and wherein the reaction REAC2 excludes perfluoroalkyl iodide.

2. The method according to claim 1, wherein BAS is selected from the group consisting of $K_3PO_4$, $K_2CO_3$, $Cs_2CO_3$, KOH, KOtBu, and DBU.

3. The method according to claim 1, wherein R3 is $C_{1-15}$ alkylene, wherein in the alkylene chain at least one of the hydrogens is substituted by F.

4. The method according to claim 1, wherein X1 is Br or I.

5. The method according to claim 1, wherein X2 is $C(O)$—$OC_{1-4}$ alkyl, F or Br.

6. The method according to claim 1, wherein the alkylene, that is represented by R3, wherein in the alkylene chain at least one of the hydrogens is substituted by F, is a perfluoroalkylene.

7. The method according to claim 1, wherein ENAM is a compound of formula (ENAM-I);

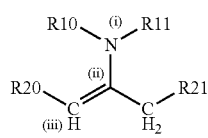

(ENAM-I)

wherein the N atom depicted with (i) is a tertiary, non-aromatic N atom;

the C atoms depicted with (ii) and (iii) are non-aromatic C atoms;

R20 and R21 are identical or different and selected from the group consisting of H, $C_{1-10}$ alkyl, $C(O)$—$C_{1-4}$ alkyl, COOH, $C(O)$—O—$C_{1-4}$ alkyl;

or

R20 and R21 form together with the 3 C atoms in $-C^{(iii)}H=C^{(ii)}(N^{(i)}(R10)R11)$-$CH_2$—, which connect R20 and R21 and with (i), (ii) and (iii) as defined herein, a 5, 6 or 7 membered carbocyclic or heterocyclic, non-aromatic ring RINGA;

the 5 membered RINGA being a ring RINGA-V as depicted in formula (RINGA-V), the 6 membered RINGA being a ring RINGA-VI as depicted in formula (RINGA-VI), and the 7 membered RINGA being a ring RINGA-VII as depicted in formula (RINGA-VII);

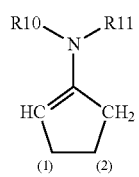

(RINGA-V)

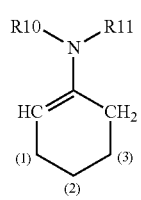

(RINGA-VI)

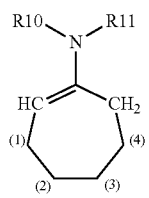

(RINGA-VII)

wherein each of the two endocyclic C atoms depicted with (1) and (2) in case of RINGA-V, each of the three endocyclic C atoms depicted with (1), (2) and (3) in case of RINGA-VI, and each of the four endocyclic C atoms depicted with (1), (2), (3) and (4) in case of RINGA-VII may be exchanged for a heteroatom O, N or S, said N may be unsubstituted or substituted by a substituent selected from the group consisting of $C_{1-10}$ alkyl, $C(O)$—$C_{1-4}$ alkyl, and phenyl;

any of the bonds connecting the endocyclic atoms depicted with (1), (2), (3) or (4) in RINGA-V, RINGA-VI and RINGA-VII respectively may be a single or a double bond;

any of the endocyclic C atoms depicted with (1), (2), (3) or (4) in RINGA-V, RINGA-VI and RINGA-VII respectively may be unsubstituted or substituted by one or two identical or different substituents selected from the group consisting of $C_{1-10}$ alkyl, $C(O)$—$C_{1-4}$ alkyl, COOH, $C(O)$—O—$C_{1-4}$ alkyl, CN, phenyl, N(R12)R13, and oxo, or may be a carbonyl protected with ethylene glycol;

the two endocyclic C atoms depicted with (1) and (4) in RINGA-VII may be connected by —$CH_2$— or by —N(R30)-;

R30 is $C_{1-4}$ alkyl, phenyl or benzyl;

R12 and R13 are identical or different and selected from the group consisting of H, $C_{1-10}$ alkyl, phenyl, and $C(O)$—$C_{1-4}$ alkyl;

or

R20 and R21 together with the 3 C atoms in the —$C^{(iii)}H=C^{(ii)}(N^{(i)}(R10)R11)$-$CH_2$— of formula (ENAM-I), which connect R20 and R21 and with (i), (ii) and (iii) as defined herein, are part of a steroid ring system;

R10 and R11 are identical or different and selected from the group consisting of $C_{1-10}$ alkyl and phenyl;

or

R10 and R11 form together with the N atom, which connects R10 and R11, a 5, 6 or 7 membered heterocyclic, non-aromatic ring RINGB;

the 5 membered RINGB being a ring RINGB-V as depicted in formula (RINGB-V), the 6 membered RINGB being a ring RINGB-VI as depicted in formula (RINGB-VI), and the 7 membered RINGB being a ring RINGB-VII as depicted in formula (RINGB-VII);

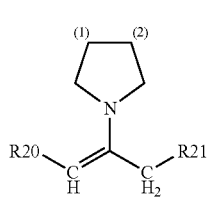

(RINGB-V)

-continued

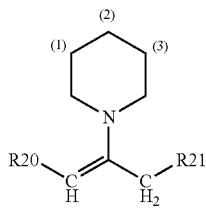
(RINGB-VI)

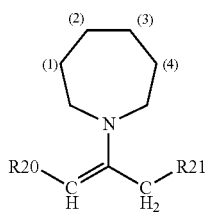
(RINGB-VII)

wherein
each of the two endocyclic C atoms depicted with (1) and (2) in case of RINGB-V,
each of the three endocyclic C atoms depicted with (1), (2) and (3) in case of RINGB-VI, and
each of the four endocyclic C atoms depicted with (1), (2), (3) and (4) in case of RINGB-VII
may be exchanged for a heteroatom O, N or S said N may be unsubstituted or substituted by a substituent selected from the group consisting of $C_{1-10}$ alkyl, $C(O)$—$C_{1-4}$ alkyl, and phenyl;
any of the bonds connecting the endocyclic atoms depicted with (1), (2), (3) or (4) in RINGB-V, RINGB-VI and RINGB-VII respectively may be a single or a double bond;
any of the endocyclic C atoms depicted with (1), (2), (3) or (4) in RINGB-V, RINGB-VI and RINGB-VII respectively may be unsubstituted or substituted by one or two identical or different substituents selected from the group consisting of $C_{1-10}$ alkyl, $C(O)$—$C_{1-4}$ alkyl, COOH, $C(O)$—O—$C_{1-4}$ alkyl, CN, phenyl, N(R14)R15, and oxo, or may be a carbonyl protected with ethylene glycol;
R14 and R15 are identical or different and selected from the group consisting of H, $C_{1-10}$ alkyl, phenyl, and $C(O)$—$C_{1-4}$ alkyl.

8. The method according to claim 7, wherein
when R20 and R21 together with the 3 C atoms in the —$C^{(iii)}$H=$C^{(ii)}$ (N$^{(i)}$(R10)R11)-CH$_2$— of formula (ENAM-I), which connect R20 and R21, are part of a steroid ring system, the steroid ring system has gonane as steroid nucleus with a carbonyl (oxo substituent) at C-3.

9. The method according to claim 1, wherein
ENAM is prepared with a reaction REAC1 of a secondary amine SEKAM with a ketone KET.

10. The method according to claim 9, wherein
SEKAM is a compound of formula (SEKAM);

(SEKAM)

wherein
the N atom depicted with (i) is a secondary, non-aromatic N atom.

11. The method according to claim 9, wherein
SEKAM is a compound of formula (SEKAM-I);

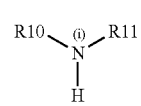
(SEKAM-I)

wherein
the N atom depicted with (i) is a secondary, non-aromatic N atom;
R10 and R11 are identical or different and selected from the group consisting of $C_{1-10}$ alkyl and phenyl;
or
R10 and R11 form together with the N atom, which connects R10 and R11, a 5, 6 or 7 membered heterocyclic, non-aromatic ring RINGB;
the 5 membered RINGB being a ring RINGB-V as depicted in formula (RINGB-V),
the 6 membered RINGB being a ring RINGB-VI as depicted in formula (RINGB-VI), and
the 7 membered RINGB being a ring RINGB-VII as depicted in formula (RINGB-VII);

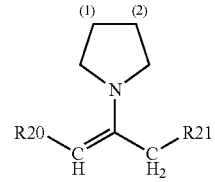
(RINGB-V)

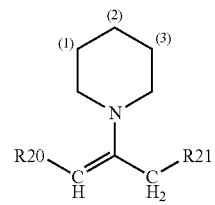
(RINGB-VI)

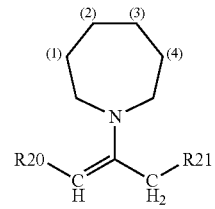
(RINGB-VII)

wherein
each of the two endocyclic C atoms depicted with (1) and (2) in case of RINGB-V,
each of the three endocyclic C atoms depicted with (1), (2) and (3) in case of RINGB-VI, and
each of the four endocyclic C atoms depicted with (1), (2), (3) and (4) in case of RINGB-VII may be exchanged for a heteroatom O, N or S said N may be unsubstituted or substituted by a substituent selected from the group consisting of $C_{1-10}$ alkyl, $C(O)$—$C_{1-4}$ alkyl, and phenyl;

any of the bonds connecting the endocyclic atoms depicted with (1), (2), (3) or (4) in RINGB-V, RINGB-VI and RINGB-VII respectively may be a single or a double bond;

any of the endocyclic C atoms depicted with (1), (2), (3) or (4) in RINGB-V, RINGB-VI and RINGB-VII respectively may be unsubstituted or substituted by one or two identical or different substituents selected from the group consisting of $C_{1-10}$ alkyl, C(O)—$C_{1-4}$ alkyl, COOH, C(O)—O—$C_{1-4}$ alkyl, CN, phenyl, N(R14)R15, and oxo, or may be a carbonyl protected with ethylene glycol.

12. The method according to claim 9, wherein KET is a compound of formula (KET);

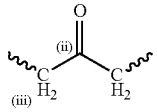

(KET)

wherein
the C atoms depicted with (ii) and (iii) are non-aromatic C atoms.

13. The method according to claim 9, wherein KET is a compound of formula (KET-I);

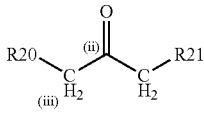

(KET-I)

wherein
the C atoms depicted with (ii) and (iii) are non-aromatic C atoms;

R20 and R21 are identical or different and selected from the group consisting of H, $C_{1-10}$ alkyl, C(O)—$C_{1-4}$ alkyl, COOH, C(O)—O—$C_{1-4}$ alkyl;

or

R20 and R21 form together with the 3 C atoms in-$C^{(iii)}$H=$C^{(ii)}$($N^{(i)}$(R10)R11)-CH$_2$—, which connect R20 and R21 and with (i), (ii) and (iii) as defined herein, a 5, 6 or 7 membered carbocyclic or heterocyclic, non-aromatic ring RINGA;

the 5 membered RINGA being a ring RINGA-V as depicted in formula (RINGA-V), the 6 membered RINGA being a ring RINGA-VI as depicted in formula (RINGA-VI), and the 7 membered RINGA being a ring RINGA-VII as depicted in formula (RINGA-VII);

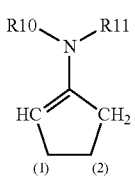

(RINGA-V)

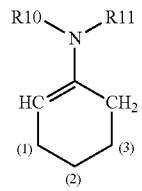

(RINGA-VI)

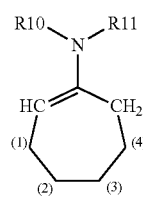

(RINGA-VII)

wherein
each of the two endocyclic C atoms depicted with (1) and (2) in case of RINGA-V, each of the three endocyclic C atoms depicted with (1), (2) and (3) in case of RINGA-VI, and each of the four endocyclic C atoms depicted with (1), (2), (3) and (4) in case of RINGA-VII may be exchanged for a heteroatom O, N or S, said N may be unsubstituted or substituted by a substituent selected from the group consisting of $C_{1-10}$ alkyl, C(O)—$C_{1-4}$ alkyl, and phenyl;

any of the bonds connecting the endocyclic atoms depicted with (1), (2), (3) or (4) in RINGA-V, RINGA-VI and RINGA-VII respectively may be a single or a double bond;

any of the endocyclic C atoms depicted with (1), (2), (3) or (4) in RINGA-V, RINGA-VI and RINGA-VII respectively may be unsubstituted or substituted by one or two identical or different substituents selected from the group consisting of $C_{1-10}$ alkyl, C(O)—$C_{1-4}$ alkyl, COOH, C(O)—O—$C_{1-4}$ alkyl, CN, phenyl, N(R12)R13, and oxo, or may be a carbonyl protected with ethylene glycol;

the two endocyclic C atoms depicted with (1) and (4) in RINGA-VII may be connected by —CH$_2$— or by —N(R30)-;

R30 may be $C_{1-4}$ alkyl, phenyl or benzyl;

R12 and R13 are identical or different and selected from the group consisting of H, $C_{1-10}$ alkyl, phenyl, and C(O)—$C_{1-4}$ alkyl;

or

R20 and R21 together with the 3 C atoms in the —$C^{(iii)}$H=$C^{(ii)}$($N^{(i)}$(R10)R11)-CH$_2$— of formula (ENAM-I), which connect R20 and R21 and with (i), (ii) and (iii) as defined herein, are part of a steroid ring system.

14. The method according to claim 9, wherein REAC1 and REAC2 are done without intermediate isolation of ENAM.

15. The method according to claim 1, wherein after REAC2, the fluoroalkylated ENAM is hydrolyzed with water in a reaction REAC3 to provide a secondary amine SEKAM and a flouralkylated ketone KET.

16. The method according to claim 15, wherein REAC3 is done under acidic conditions.

17. The method according to claim 15, wherein REAC2 and REAC3 are done without intermediate isolation of the fluoroalkylated ENAM after REAC2.

18. The method according to claim 15, wherein REAC1, REAC2 and REAC3 are done without intermediate isolation of ENAM or of the fluoroalkylated ENAM.

* * * * *